US012692278B2

(12) United States Patent
Deslauriers et al.

(10) Patent No.: US 12,692,278 B2
(45) Date of Patent: Jul. 28, 2026

(54) SYNTHESIS METHODS AND COMPOSITIONS OF LOW INTERMEDIATE AND LOW DICHELATE INTERMEDIATE CONTRAST AGENTS

(71) Applicant: Inventure, LLC, Southbury, CT (US)

(72) Inventors: Richard J. Deslauriers, Woodbury, CT (US); Michael Milbocker, Holliston, MA (US); Paul Lombardo, Stamford, CT (US)

(73) Assignee: INVENTURE, LLC, Southbury, CT (US)

( * ) Notice: Subject to any disclaimer, the term of this patent is extended or adjusted under 35 U.S.C. 154(b) by 1150 days.

(21) Appl. No.: 17/590,549

(22) Filed: Feb. 1, 2022

(65) Prior Publication Data

US 2022/0242885 A1    Aug. 4, 2022

Related U.S. Application Data

(60) Provisional application No. 63/144,291, filed on Feb. 1, 2021, provisional application No. 63/144,346, filed on Feb. 1, 2021, provisional application No. 63/144,299, filed on Feb. 1, 2021.

(51) Int. Cl.
  *C07F 5/00*        (2006.01)
  *A61K 51/04*        (2006.01)

(52) U.S. Cl.
  CPC .......... *C07F 5/003* (2013.01); *A61K 51/0482* (2013.01)

(58) Field of Classification Search
  CPC .... A61K 51/00; A61K 51/04; A61K 51/0482; A61K 49/00; A61K 49/108; C07F 5/003
  See application file for complete search history.

(56) References Cited

U.S. PATENT DOCUMENTS

| | | | |
|---|---|---|---|
| 5,494,656 A | 2/1996 | Davies | |
| 6,143,274 A | 11/2000 | Tweedle et al. | |
| 6,303,761 B1 | 10/2001 | Wang | |
| 7,012,140 B1 | 3/2006 | Sherry | |
| 7,767,196 B2 | 8/2010 | Wong et al. | |
| 9,458,117 B2 * | 10/2016 | Buffel | C07D 457/04 |
| 9,579,404 B2 | 2/2017 | Walters | |
| 9,907,866 B2 | 3/2018 | Meyer et al. | |
| 10,064,961 B2 | 9/2018 | Welzig | |
| 10,245,328 B2 | 4/2019 | Kim et al. | |
| 10,314,927 B2 | 6/2019 | Thaning et al. | |
| 10,556,873 B2 | 2/2020 | Chong | |
| 10,576,169 B2 | 3/2020 | Thaning et al. | |
| 10,653,804 B2 | 5/2020 | Deslauriers et al. | |
| 10,941,124 B2 * | 3/2021 | Meijer | B01D 9/0054 |
| 11,186,553 B2 | 11/2021 | Thaning et al. | |
| 11,370,804 B2 | 6/2022 | Le Greneur et al. | |
| 11,419,953 B2 | 8/2022 | Deslauriers et al. | |
| 11,590,246 B2 | 2/2023 | Greneur et al. | |
| 11,944,690 B2 | 4/2024 | Holzschuh et al. | |

| | | | |
|---|---|---|---|
| 12,036,289 B2 | 7/2024 | Napolitano et al. | |
| 2006/0057071 A1 | 3/2006 | Wong et al. | |
| 2007/0098643 A1 | 5/2007 | Nachman | |
| 2011/0129425 A1 | 6/2011 | Meyer | |
| 2011/0274624 A1 | 11/2011 | Decuzzi | |
| 2016/0051706 A1 | 2/2016 | Buffel et al. | |
| 2017/0216462 A1 | 8/2017 | Welzig et al. | |
| 2017/0258944 A1 | 9/2017 | Thaning et al. | |
| 2018/0185521 A1 * | 7/2018 | Deslauriers | A61K 49/1806 |
| 2019/0031640 A1 | 1/2019 | Martins | |
| 2019/0269805 A1 | 9/2019 | Deslauriers | |
| 2019/0365933 A1 | 12/2019 | Deslauriers et al. | |
| 2020/0155712 A1 | 5/2020 | Thaning | |
| 2020/0390910 A1 | 12/2020 | Welzig et al. | |
| 2021/0283278 A1 | 9/2021 | Law et al. | |
| 2022/0080058 A1 | 3/2022 | Deslauriers | |
| 2022/0242885 A1 | 8/2022 | Deslauriers et al. | |
| 2022/0370646 A1 | 11/2022 | Baranyai et al. | |
| 2022/0387634 A1 | 12/2022 | Deslauriers et al. | |
| 2023/0025866 A1 | 1/2023 | Thaning et al. | |
| 2024/0189459 A1 | 6/2024 | Deslauriers et al. | |
| 2025/0041460 A1 | 2/2025 | Deslauriers et al. | |

FOREIGN PATENT DOCUMENTS

| | | |
|---|---|---|
| CN | 101977633 B | 8/2012 |
| CN | 109336833 B | 9/2020 |
| DE | 3129906 A1 | 2/1983 |
| EP | 3 315 141 A1 | 5/2018 |

(Continued)

OTHER PUBLICATIONS

Alpoim et al . Determination of the number of inner-sphere water molecules in lanthanide ( III ) polyaminocarboxylate complexes . 1992 J. Chem . Soc . Dalton Trans . 3 : 463-467 . ( Year : 1992 ).

Brown, "Effects of the Operating Magnetic Field on Potential NMR Contrast Agents" (1985) Magnetic Resonance Imaging, vol. 3, pp. 3-9.

Gazzi et al: "A greener approach toward gadolinium-based contrast agents", RSC Adv., vol. 4, No. 19, Jan. 1, 2014 (Jan. 1, 2014), pp. 9880-9884.

Jeong et al., "Synthesis of a gadolinium based-macrocyclic MRI contrast agent for effective cancer diagnosis," Biomaterials Research (2018) 22:17.

(Continued)

*Primary Examiner* — D. L. Jones

(74) *Attorney, Agent, or Firm* — Ruggiero McAllister & McMahon LLC

(57) ABSTRACT

Macrocyclic gadolinium-based contrast agents (GCA) are synthesized by pathways characterized by the formation of a sequence of metastable complexes before obtaining the final stable complex. Commercial macrocyclic GCAs contain unstable metastable complexes. These metastable species quickly release free Gd3+ ions upon delivery into the body. Aqueous or dry/solid GCA with near zero metastable species content and methods of synthesizing the same are disclosed.

22 Claims, 7 Drawing Sheets

(56) References Cited

FOREIGN PATENT DOCUMENTS

| | | |
|---|---|---|
| EP | 3363466 A1 | 8/2018 |
| EP | 3 315 141 B1 | 10/2020 |
| EP | 4 335 462 A1 | 3/2024 |
| EP | 4 335 840 A1 | 3/2024 |
| FR | 2927539 A1 | 8/2009 |
| KR | 101513767 B1 | 4/2015 |
| KR | 101625656 B1 | 5/2016 |
| KR | 101646211 B1 | 8/2016 |
| WO | 2009/103744 A2 | 8/2009 |
| WO | 2012/143355 A1 | 10/2012 |
| WO | 2016015066 A1 | 2/2016 |
| WO | 2016/083597 A1 | 6/2016 |
| WO | 2016083605 A1 | 6/2016 |
| WO | 2017046694 A1 | 3/2017 |
| WO | 2018/054340 A1 | 3/2018 |
| WO | 2020/012372 A1 | 1/2020 |
| WO | 2022035969 A1 | 2/2022 |

OTHER PUBLICATIONS

Runge et al., "Paramagnetic Agents for Contrast-Enhanced NMR Imaging: A Review" (1983) American Journal of Radiology, vol. 141, pp. 1209-1215.

Schmitt-Willich et al., "Synthesis and Physicochemical Characterization of a New Gadolinium Chelate: The Liver-Specific Magnetic Resonance Imaging Contrast Agent Gd-EOB-DTPA" Inorganic Chemistry (1999), vol. 38, pp. 1134-1144.

Weinman et al., "Characteristics of Gadolinium-DTPA Complex: A Potential NMR Contrast Agent" (1984) American Journal of Radiology, vol. 142, pp. 619-624.

Anderegg, Giorgio, Arnaud-Neu, Francoise, Delgado, Rita, Felcman, Judith and Popov, Konstantin. "Critical evaluation of stability constants of metal complexes of complexones for biomedical and environmental applications* (IUPAC Technical Report)" Pure and Applied Chemistry, vol. 77, No. 8, 2005, pp. 1445-1495.

Cacheris, W. P. et al.; "Thermodynamic Study of Lanthanide Complexes of 1,4,7-Trazacyclononane-N,N',N"-triacetic Acid and 1,4,7,10-Tetraazacyclododecane-N,N',N",N'''-tetraacetic Acid", Inorganic Chemistry, vol. 26, No. 6, 1987, pp. 958-960.

Stasiuk, Graeme J. et al.; "The ubiquitous DOTA and its derivatives: the impact of 1,4,7,10-tetraazacyclododecane-1,4,7,10-tetraacetic acid on biomedical imaging", Chem. Commun., 2013, 49, pp. 2732-2746.

Toth, E. et al.; "Stability constants of the lanthanide(III)-1,4,7,10-tetraazacyclododecane-N,N', N", N'''-tetraacetate complexes", Inorganica Chimica Acta, 221, 1994, pp. 165-167.

Sieving, P.F. et al; Preparation and Characterization of Paramagnetic Polychelates and Their Protein Conujugates; Bioconjugate Chemistry, vol. 1, No. 1, 1990, pp. 65-71.

Caravan et al.; "Molecular Factors That Determine Curie Spin Relaxation in Dysprosium Complexes"; Magnetic Resonance in Medicine; 46:917-922, 2001.

Kotek et al.; "Synthesis and Characterization of Ligands and their Gadolinium(III) Complexes"; The Chemistry of Contrast Agents in Medical Magentci Resonanace Imaging, 2013, pp. 84-155.

Morel et al.; "NMR relaxometric investigations of solid lipid nanoparticles (SLN) containing gadolinium(III) complexes"; European Journal of Pharmaceutics and Biopharmaceutics 45, (1998) 157-163.

International Search Report dated May 11, 2022 for PCT Appl. No. PCT/US2022/014754.

Written Opinion Report dated May 11, 2022 for PCT Appl. No. PCT/US2022/014754.

Marshall, J.L., A Living Periodic Table, J. Chem. Ed., 2000; 77:979-983. (Year: 2000).

Brooks, K.P.; et al., Assessment of Commercially Available Ion Exchange Materials for Cesium Removal from Highly Alkaline Wastes, Department of Energy, 1996; 1-63. (Year: 1996).

Mitsubishi Chemical Corporation, Product Data Sheet for Diaion CR11, Document Number 01-09-A-0104, 2017; 1-3. (Year: 2017).

Ahern, K. and Rajagopal, L., Ion Exchange Chromatography, LibreTexts Chemistry, 2022; 1-4. (Year: 2022).

* cited by examiner

SYNTHESIS METHODS AND COMPOSITIONS OF LOW INTERMEDIATE AND LOW DICHELATE INTERMEDIATE CONTRAST AGENTS

CROSS REFERENCE TO RELATED APPLICATIONS

This application claims the benefit of U.S. Provisional Application Ser. Nos. 63/144,291, 63/144,299, and 63/144,346, each filed Feb. 1, 2021, the entire contents of each of which is incorporated by reference herein.

BACKGROUND OF THE DISCLOSURE

1. Field of the Disclosure

The present disclosure relates to macrocyclic MRI contrast agents. More particularly, the present disclosure relates to synthesis methods and compositions of low intermediate and low dichelate intermediate contrast agents

2. Brief Description of Related Art

Lanthanide series metal-based contrast agents are injectables capable of enhancing a biologic image obtained by magnetic resonance imaging (MRI). MRI detects the nuclear magnetic resonance of the proton in the hydrogens contained in a molecule of water. Images are formed by spatially measuring the resonance, which varies by water density and tissue type. The image signal is derived from the spins of the protons, whose spin are preferentially aligned with a static magnetic, homogeneous field.

The aligned protons are in a lower energy state than misaligned protons. When an RF pulse at resonant frequency (5 to 100 MHz) is applied to spin aligned protons, the low energy photons absorb that RF energy causing the proton spins to flip. Referring to FIG. 1, a schematic of the dynamical proton spin 101 during the MRI process 100 comprises alignment of proton spin with an external magnetic field 102, randomization of the alignment 104, and subsequent release of energy 106 comprising the signal of the MRI and return to the aligned state 108. The transition time from randomized state 104 to aligned state 108 is called the $T_1$ time 109. The transition time from the aligned state 102 to the randomized state 104 is called the $T_2$ time 111.

The $T_2$ signal involves absorption of the RF energy 110 by the aligned protons 102 which flips the proton spin 112. The combination of oriented 114 and counter-oriented 112 spins generates a combined spin vector in the xy-plane 116. The result is a spin moment vector 116 in the plane perpendicular 118, $M_{xy}$, to the direction of the magnetic field 120, $M_z$.

The $T_1$ signal involves emission of RF energy 122 by the spin randomized protons 104. When the RF pulse 110 stops, the proton spins relax back to their lower energy aligned state 102, releasing radio waves 122 comprising the image. The faster this transition occurs, $T_1$, the higher the intensity (energy per unit time) of the image signal.

Macrocyclic gadolinium-based MRI contrast agents (GCAs) reduce $T_1$ and increase image quality by placing some of the protons of ambient water molecules inside a coordination cage. The coordination complex generates a reference frame for the protons. The equilibrium orientation of the complex is in the direction of the magnetic field, and the complex orientation is not randomized by the RF pulse. When the photon is energized by the RF pulse, it must resist the orientation of the coordination complex, which causes the spin to snap back to the aligned position faster than the protons of a free water molecule when the RF energy stops.

Coordination complexes are ubiquitous emergent structures with their own physical and chemical properties, many of which are confusingly complex. Coordination complexes are in a sense a distinct phase of matter, the molecular equivalent of the macroscopic crystalline state. The coordination complex results from the charge complementarity of a positively charged metal ion and the negatively charged groups of a ligand molecule. The coordination complex is characteristically dynamical. The coordination bonds comprising the complex are reversible and metastable between covalent bonding and ionic bonding.

The atom within a ligand that is bonded to the central metal atom or ion is called the donor atom. In a typical coordination complex, a metal ion is bonded to several donor atoms. For example, a complex of Gd3+ ion and DOTA comprises 8 donor atoms, 4 of which are the nitrogen atoms of amine groups and 4 are the oxygen atoms of carboxylate groups. These complexes are called chelate complexes; the formation of such complexes is called chelation, complexation, and coordination.

Referring to FIG. 2, the gadoterate meglumine (Gd-DOTA) coordination complex 200 comprises ligand 202 (DOTA) and Gd3+ ion 204 and coordination bonds 206. Gadolinium has 9 possible coordination bonds, eight of which include the coordination bonds. The ninth bond 207 holds the $T_1$ reduced water molecule 208. This water molecule exchanges rapidly with ambient water without destabilizing the coordination complex 200. In this way, the Gd-DOTA complex can enhance the $T_1$ time for many water molecules. The coordination bonds are between the Gd3+ ion 204 and the oxygen atoms 210 of carboxylate groups on ligand 202 and the nitrogen atoms 212 of amine groups on ligand 202. Metastable intermediates of the coordination complex include states where one or more of the eight coordination bonds is broken and the negatively charged ligand groups 210 and 212 form bonds with the positively charged hydrogens of ambient water molecules. Before reaction of the ligand 202 with the metal ion 204 one or more of the ligand bonding sites 210 and 212 are occupied by water molecules. These water molecules are called hydration molecules. Formation of the coordination complex 200 involves removing these water molecules and replacing them with coordination sites on the Gd3+ ion 204. The hydration molecules of a metastable form complex or metastable intermediate do not participate in $T_1$ reduction since they are not centrally located and constrained by the enveloping effect of the ligand.

The central atom or ion, together with all ligands, comprise the coordination sphere. The central atoms or ion and the donor atoms comprise the first coordination sphere. Referring to FIG. 3, the coordination sphere 300 comprises first coordination sphere 302 which comprises the eight coordination bonds 304 between Gd3+ ion 308 and ligand groups 310, and the coordination water 306. The Gd3+ ion 308 resides centrally in the first coordination sphere 302. Coordination water 306 readily exchanges 311 with ambient water 312. The second sphere 314 comprises an outer region 316 where the Gd3+ ion 308 resides in the metastable complex or intermediate state. The peripheral location of Gd3+ ion 308 is responsible for the instability of metastable complex or intermediate states. A third outer sphere 318 comprising oriented water molecules 320 responsible for stabilizing the orientation of the coordinate complex 322.

Coordination refers to the "coordinate covalent bonds" (dipolar bonds) between the ligands and the central atom. By complex one means a reversible association of molecules, atoms, or ions through weak chemical bonds that are unique to the coordination phase of matter. The coordination aspect is usually more important than the complex aspect, and as such coordination complexes refer to a wide class of charge complimentary conformations where the bond strength varies from practically irreversible, to a collection of conformations embodied as a single dynamical coordination state. For example, several isomers of coordination configurations can comprise a single coordination complex. Consequently, formation of the coordinate complex, a subject of the present disclosure, depends sensitively on ambient reaction conditions, and several metastable intermediate forms are known. By metastable intermediate form of a given metal ion-ligand combination one means any coordination complex which is not the minimal energy coordination complex. The minimal energy coordination complex is called the final coordination complex. All metastable complexes or metastable intermediates are unstable and can dissociate to either the free ionic form or transform ultimately to the final coordination complex. When there is an energy barrier between the final coordination complex and a metastable intermediate coordination complex, generally the metastable intermediate coordinate complex degrades to the free ionic form. This energy barrier exists for the Gd-DOTA coordination complex and many other macrocyclic GCAs, and is primarily responsible for detectable levels of free Gd3+ ion in commercial macrocyclic GCAs.

The number of donor atoms attached to the central atom or ion is called the coordination number. A hydrated ion is one kind of a complex ion, and a species formed between a central metal ion and one or more surrounding ligands, molecules or ions that contain at least one lone pair of electrons. Metastable intermediate coordinate complexes contain hydrated ligand coordination groups.

A donor atom is an atom that gives a pair of electrons to a positively charged metal ion. There are some donor atoms or groups which can offer more than one pair of electrons. In some cases an atom or a group offers a pair of electrons to two similar or different central metal atoms or acceptors into a three-center two-electron bond. These types of exotic bonds which characterize uniquely coordination complexes are called bridging ligands.

The lanthanide series of elements, when hydrated, fall into a category called "hard" acids where bonding with other elements is considered largely ionic or electrostatic, even though these bonds are sometimes considered covalent.

Gd3+ ion is desirable as an image enhancement ion because of its favorable paramagnetic properties. However, Gd3+ ion is highly toxic. The toxicity of Gd3+ is due to its central position in the lanthanide series, with an ionic radius of 0.99 Å, very nearly equal to that of divalent Ca2+. This is one of the reasons why Gd3+ is so toxic in biological systems. Gd3+ competes with Ca2+ in all biological systems that require Ca2+ for proper function. The trivalent ion Gd+ binds with much higher affinity than the divalent ion Ca2+. When Gd3+ binds to a Ca2+ binding enzyme, the kinetics of the biological process catalyzed by that enzyme is severely compromised.

Gd3+ exists in aqueous solution in several hydration forms. Below pH 6 Gd3+ is hydrated with 8 or 9 first coordination sphere water molecules. Upon chelation by an organic ligand such as those used in clinically approved MRI contrast agents, the water molecules must be displaced from the first coordination sphere of the Gd3+ ion by the more basic donor atoms of the ligand, typically amines (N) or carboxylates (O). A typical ligand used to create MRI contrast agents has eight donor atoms. Upon chelation, a single water molecule remains in the first coordination sphere of the Gd3+. This single water binding site is important for MRI contrast because it allows, through chemical exchange, a large number of water molecules to have reduced $T_1$ time. When greater than one water molecule is present in the first coordination sphere the number of water molecules enhanced by $T_1$ reduction is significantly reduced. Interestingly, because metastable intermediate complexes are relatively rarely formed, typically less than 1 in the final product, the existence of metastable intermediate forms has been largely ignored. However, the propensity for metastable intermediate forms to release in vivo free Gd3+ ion makes the metastable intermediate forms a serious health threat at levels far below 1%.

Accordingly, it has been determined by the present disclosure that there is a continuing need for an MRI contrast agent that overcomes, alleviates, and/or mitigates one or more of the aforementioned and other deleterious effects of prior devices.

SUMMARY OF THE DISCLOSURE

The present disclosure has surprising found that the kinetic stability and, therefore, the level of free Gd in the final drug product (e.g., gadoterate meglumine) in vial and, particularly, in-vivo, is a function of the amount of metastable intermediate compounds (impurities) in the product.

The first family of metastable intermediate compounds (impurities) are partially alkylated cyclen molecules as well as dimers of these molecules and/or DOTA. When gadolinium oxide is added to these compounds, the acid-base reaction is quick and irreversible impurities that are much less kinetically stable are formed.

The second family of metastable intermediate compounds (impurities) are complexation intermediates that result from adding meglumine before all molecules have had time to attain their most stable complexation state. The most stable gadoterate meglumine molecule results when the Gd is bound either chemically or covalently in nine locations. The formation of the most stable coordination state takes significant reaction time. If the reaction or final product is checked by standard analytical techniques such as HPLC, the reaction will appear to be complete in a few hours since the acid-base reaction of DOTA and gadolinium oxide is fast and all of the metastable intermediates have the same molecular weight and formula as the fully complexed final product. If meglumine is added at this point, full complexation and, therefore, maximum kinetic stability will not be achieved.

By monitoring the reaction in-situ with FTIR, preferentially mid-band FTIR with a diamond crystal, the full and proper complexation of this second family of metastable intermediates can be ensured. A "waterfall" plot is used to show the changing make-up of the reaction mixture. When this plot shows slowing or little change, it is determined that the most stable complex dominates the mixture. At this point, the meglumine is added. When this pure final drug product is injected into the body the release of free gadolinium is 2 to 3 orders of magnitude lower than existing commercial products Additionally or alternately, an improved version of the xylenol orange titration of free Gd3+ in the USP can be used as both an in-process check and a final product check. To obtain a limit of detection adequate for the product produced in the above claims, UV spectroscopy must be used in conjunction with the titration to measure the xylenol orange/ free Gd reaction. Furthermore, an indirect measure of metastable intermediates is obtained when the titration reaction is allowed to proceed past the initial reaction of xylenol orange and free Gd. This is because xylenol orange will pull Gd from the metastable intermediates over time. Since the fully complexed product will not give up its Gd to xylenol orange as readily, a plot of the change in the free Gd measured from 5 minutes of xylenol orange reaction time to the selected extended reaction time with xylenol orange, is an indirect measure of the quantity of meta stable intermediates. When the free Gd measured is constant or exhibits little change over the time period selected, it is determined that the metastable intermediates have been minimized and the fully complexed final product has been maximized.

The present disclosure provides methods for making a lanthanide series contrast agent. The lanthanide series contrast agent has at least one atom of a lanthanide series metal and at least one macrocyclic chelate. The lanthanide series of chemical elements comprises the 15 metallic chemical elements with atomic numbers 57-71, from lanthanum through lutetium.

For example, a method includes: (a) reacting a macrocyclic chelate with a lanthanide series metal oxide in water at a temperature and reaction time sufficient to provide a lanthanide series metal ion:macrocyclic chelate complex. In examples, the macrocyclic chelate has <10 ppm impurities containing a cyclen ring. The method further includes (b) monitoring the reaction of the macrocyclic chelate with the lanthanide series metal oxide to determine the content of metastable intermediates. Here, the metastable intermediates are partially chelated complexes. The metastable intermediates can be metal ion-ligand complexes with a coordination complex that is not the minimal energy coordination complex or metal ion-ligand complexes with minimally hydrated ligand coordination groups or both. The method further includes (c) returning to (a) if a content of metastable intermediates determined by (b) exceeds 500 parts per million. The method further includes (d) reacting the lanthanide series metal ion:macrocyclic chelate complex with a base at a temperature and reaction time sufficient to provide a complex of lanthanide series metal ion, macrocyclic chelate, and base in an aqueous formulation. The aqueous formulation has less than about 500 parts per million of metastable intermediates.

In examples, (c) returning to (a) is performed if a content of metastable intermediates determined by (b) exceeds 100 parts per million, preferably 50 parts per million, more preferably 10 parts per million, still more preferably 5 parts per million, and most preferably 1 part per million.

The method can further include, (e) monitoring the reaction of the lanthanide series metal ion:macrocyclic chelate complex with a base to determine the content of metastable intermediates and (f) returning to (d) if a content of metastable intermediates determined by (e) exceeds 500 parts per million.

In examples, (f) returning to (d) is performed if a content of metastable intermediates determined by (e) exceeds 100 parts per million, preferably 50 parts per million, more preferably 10 parts per million, still more preferably 5 parts per million, and most preferably 1 part per million.

In examples, the monitoring of the method can be performed in situ or by obtaining samples from the reactor.

In examples, the content of metastable intermediates is determined by Fourier Transform Infrared Spectroscopy, High Performance Liquid Chromatography, Ultra High Performance Liquid Chromatography, or Trans-metalation reaction. In other examples the content of metastable intermediates is determined by combinations of the foregoing. In other examples, the content of metastable intermediates is determined by an improved xylenol orange method according to the present disclosure.

In examples, the method can be performed without the use of solvents so that the method can be solvent free.

In a solvent free method according to the present disclosure, the aqueous formulation has less than about 100 parts per million of a non-aqueous solvent, preferably less than about 50 parts per million of a non-aqueous solvent, more preferably less than about 10 parts per million of a non-aqueous solvent, and most preferably less than about 1 part per million of a non-aqueous solvent.

In examples of a solvent free method, such trace amounts of solvents can result from the raw materials used.

In examples, the macrocyclic chelate is reacted with the lanthanide series metal oxide in water at a temperature from about 60° C. to about 120° C., and reaction time form about 12 hours to about 48 hours.

In examples, the reaction temperature is from about 70° C. to about 100° C., preferably from about 75° C. to about 95° C., and more preferably from about 85° C. to about 95° C.

In examples, the reaction time is from about 12 hours to about 36 hours. In other examples, the reaction time greater than about 24 hours, preferably greater than about 32 hours, more preferably greater than about 36 hours, still more preferably greater than about 42 hours, and most preferably greater than about 48 hours.

In examples, the aqueous formulation has a pH from about 7.2 to about 7.8, preferably from about 7.5 to about 7.8, and more preferably from about 7.51 to about 7.80.

In examples, the aqueous formulation has a free macrocyclic chelate concentration from about 0.0001 to about 0.0600 weight percent.

In examples, the macrocyclic chelate and the lanthanide series metal oxide are reacted in essentially stoichiometric amounts.

In examples, the aqueous formulation has less than about 50 parts per million of metastable intermediates, preferably less than about 10 parts per million of metastable intermediates, more preferably less than about 5 parts per million of metastable intermediates, and still more preferably less than about 1 part per million of metastable intermediates, and most preferably less than about 0.5 parts per million of metastable intermediates.

In examples, the lanthanide series metal ion:macrocyclic chelate complex is reacted with the base at a temperature and time until the complex is buffered to a pH of about 7.1 to about 7.6

In examples, the lanthanide series metal can be gadolinium, yttrium, europium, and combinations thereof. In preferred examples, the lanthanide series metal is gadolinium.

The macrocyclic chelate used in the methods according to the present disclosure can be diethylenetriamine-N-oxide pentaacetic acid-bisamide, 1,4,7,10-Tetraazacyclododecane-1,4,7,10-tetraacetic acid, 2-[4,7-bis(carboxylatomethyl)-10-(2-hydroxypropyl)-1,4,7,10-tetrazacyclododec-1-yl]acetate, and 2-[4,10-bis(carboxylatomethyl)-7-(1,3,4-trihydroxybutan-2-yl)-1,4,7,10-tetrazacyclododec-1-yl]acetate.

The lanthanide series metal ion:macrocyclic chelate complex in the methods according to the present disclosure can be gadolinium ion:diethylenetriamine-N-oxide pentaacetic acid-bisamide, gadolinium ion:1,4,7,10-Tetraazacyclododecane-1,4,7,10-tetraacetic acid, gadolinium ion:2-[4,7-bis(carboxylatomethyl)-10-(2-hydroxypropyl)-1,4,7,10-tetrazacyclododec-1-yl]acetate, and gadolinium ion:2-[4,10-bis(carboxylatomethyl)-7-(1,3,4-trihydroxybutan-2-yl)-1,4,7,10-tetrazacyclododec-1-yl]acetate.

In examples, the lanthanide series contrast agent can be Gd-HP-DO3A, Gd-BT-DO3A, Gd-DOTA, or Gd-diethylenetriamine-N-oxide pentaacetic acid-bisamide.

In examples, step (a) can accelerated by light at a wavelength of 400 nm to 800 nm wavelength light, a catalyst, ultrasonic sound or combinations thereof. In examples where the acceleration is by a catalyst, the catalyst can be a platinum or palladium lattice. In examples, the lattice is preferably nano scale.

In one example the base is meglumine. In other examples, the base can be meglumine, sodium hydroxide, protonated amines, water, alkynes, amines, alkanes, and combinations thereof. The base can have a pKa value greater than about 10.

In examples, removing metastable intermediates from the reaction can be by an acid-phosphate precipitation method, a negative ionic resin precipitation method, a diethylenetriaminepentacetate (DTPA) addition method, or a cage formation method.

In the cage formation method, a cyclen molecule and lanthanide series metal ion are provided. The lanthanide series metal ion is captured within the cyclen molecule. Carboxylic acid arms are sequentially added to complex with the lanthanide series metal ion, thereby forming a cage around the lanthanide series metal ion.

In examples, the reaction time is at least 24 hours, and the aqueous formulation comprises less than about 5 parts per million of metastable intermediates.

In other examples, the reaction time is at least 36 hours, and the aqueous formulation comprises less than about 1 part per million of metastable intermediates.

In examples, the aqueous formulation has a free macrocyclic chelate concentration from about 0.005 to about 0.075 weight percent.

In examples, the lanthanide series contrast agent has less than about 300 parts per million of water.

In certain examples, the method can further include controlling the content of metastable intermediates by forming bi-chelate metastable-free lanthanide series metal ion:macrocyclic chelate complexes. The lanthanide series contrast agent has less than about 500 parts per million of the bi-chelate metastable-free lanthanide series metal ion:macrocyclic chelate complexes.

In bi-chelate examples, the bi-chelate metastable-free lanthanide series metal oxide:macrocyclic chelate complexes includes DOTA-Gd-DOTA complexes.

In bi-chelate examples, the bi-chelate metastable-free lanthanide series metal oxide:macrocyclic chelate complexes are biocompatible contaminants, and not metastable intermediates.

DOTA-Gd-DOTA complexes can be formed by Gd3+ associating with two DOTA molecules, with neither DOTA molecule fully entering the coordination sphere of Gd3+.

A composition comprising: a lanthanide series contrast agent, wherein the lanthanide series contrast agent comprises at least one atom of lanthanide series metal and at least one macrocyclic chelate. The lanthanide series contrast agent can be prepared according to the methods of the present disclosure. Advantageously, such a composition a is kinetically stable, thermodynamically stable, or both kinetically and thermodynamically stable prior to clearance from the kidney of a patient.

A method for enhancing a biologic image obtained by MRI is also provided. The method includes using a lanthanide series contrast agent, that includes at least one atom of lanthanide series metal and at least one macrocyclic chelate. The lanthanide series contrast agent can be prepared according to the methods of the present disclosure.

The above summary is not intended to describe each disclosed implementation, as features in this disclosure can be incorporated into additional features as detailed herein below unless clearly stated to the contrary.

BRIEF DESCRIPTION OF DRAWINGS

The accompanying drawings illustrate aspects of the present disclosure, and together with the general description given above and the detailed description given below, explain the principles of the present disclosure. As shown throughout the drawings, like reference numerals designate like or corresponding parts.

FIG. 6 shows a resin used according to the present disclosure.

FIG. 7 illustrates construction of a DOTA macrocyclic cage around a Gd3+ ion.

DETAILED DESCRIPTION OF THE DISCLOSURE

Figure 1:
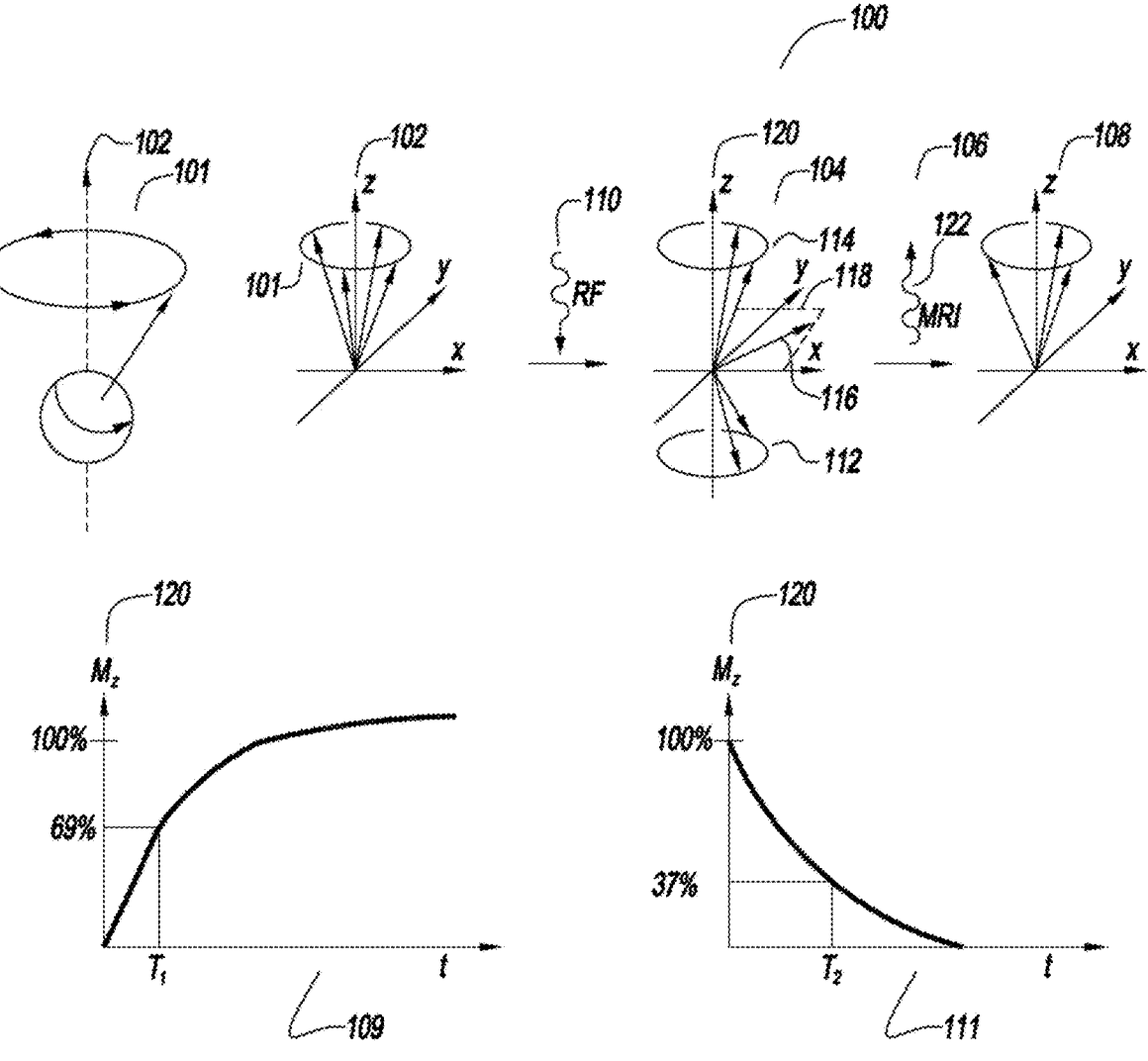
FIG. 1 is a schematic of the dynamical proton spin during the MRI process.
Figure 2:
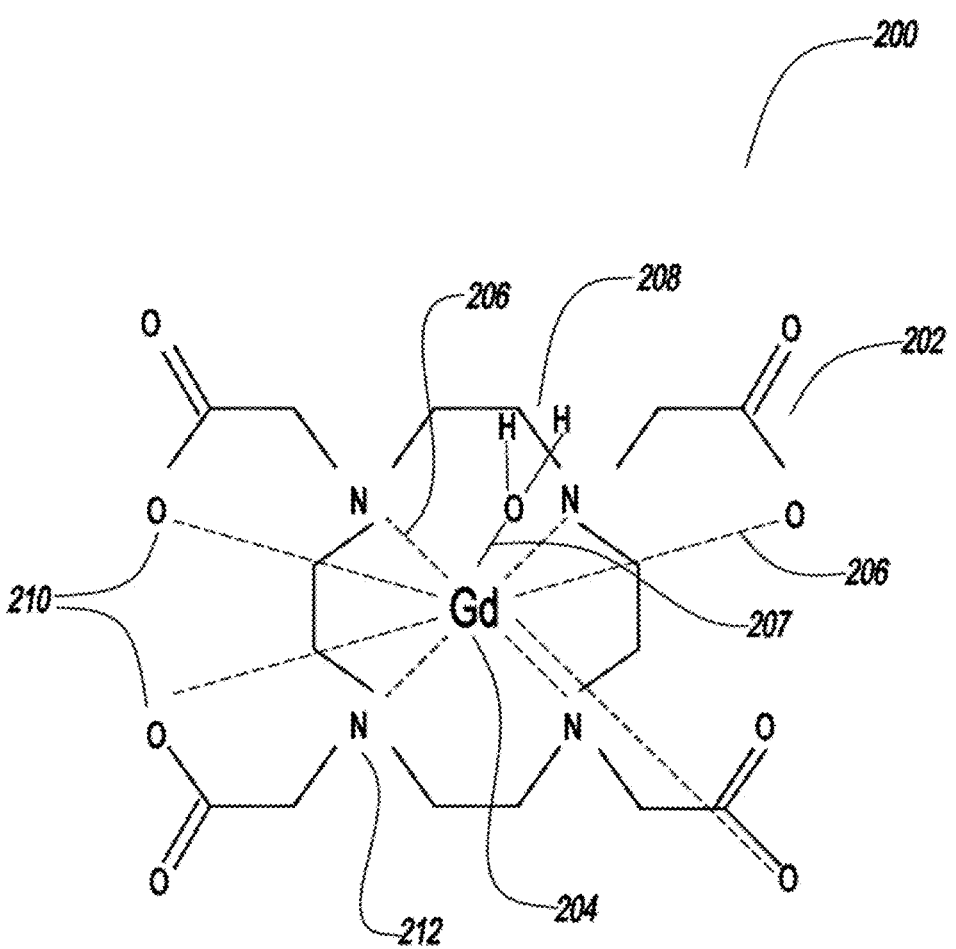
FIG. 2 shows a gadoterate meglumine (Gd-DOTA) coordination complex.
Figure 3:
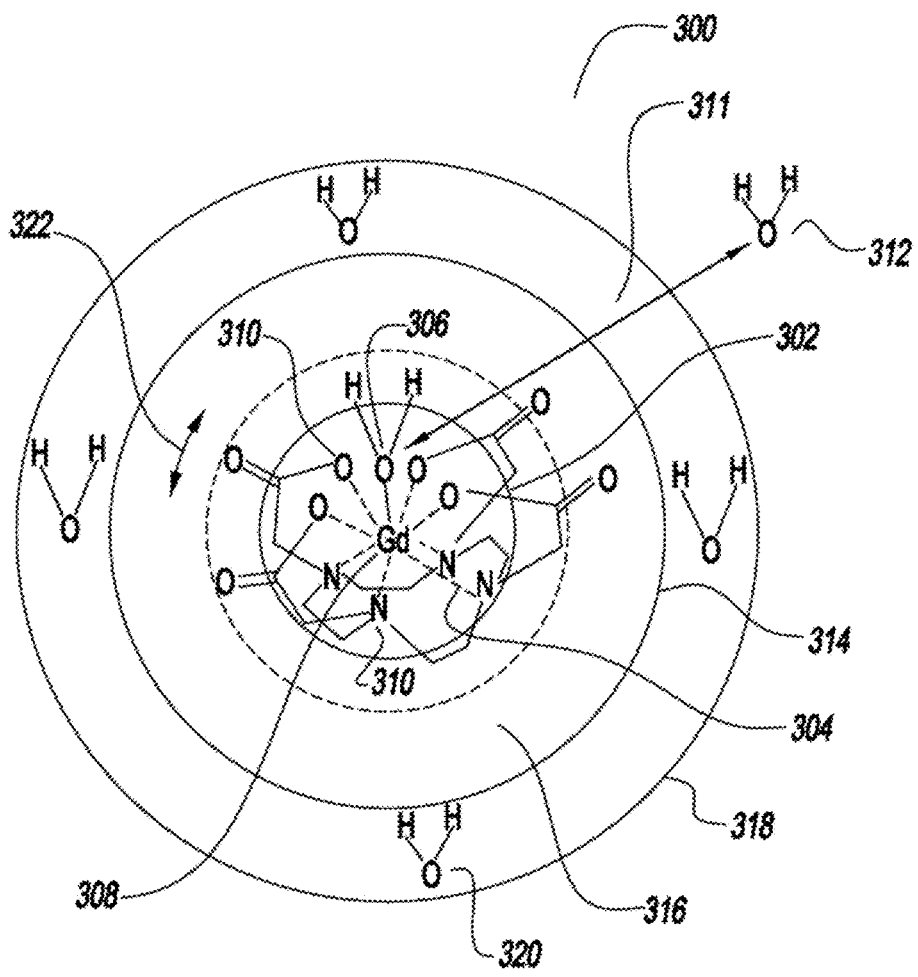
FIG. 3 shows a gadolinium coordination sphere.

The present disclosure provides a novel understanding and appreciation that changes to synthesis chemistry accounts for the differences in the coordination chemistry of linear and macrocyclic chelates (ligands). The first consideration is the rate of complex formation. The rate at which a ligand forms a complex with $Gd(H_2O)_8^{3+}$ depends upon many factors including pH, temperature, concentration of reactants and, interestingly, the structure of the ligand. The structure of the ligand determines the complexity of the reaction pathway toward a maximally stable coordination complex.

The reason free gadolinium can be more abundant for macrocyclic chelators of gadolinium is because the macrocyclics form less stable metastable intermediates or complexes with gadolinium, whereas the linear ligands form less metastable intermediates or complexes.

Potentially free gadolinium refers to those metastable intermediates or metastable complex states which technically do not have free Gd3+ ion and therefore are not detected as free, but readily release Gd3+ when introduced into the body.

The present disclosure provides novel heat synthesis methods, detection, monitoring and intermediate scavenging techniques that which reduce the presence of metastable intermediates to near zero in an aqueous or dry/solid MRI contrast agent, thus reducing the total amount of toxic free gad that is readily released in the body. As used herein in this context, because the complex is constantly chelating and de-chelating at least to a certain degree, zero and near zero means 1 part per billion so that the product is 99.999+% pure. It will be appreciated by those of skill in the art that zero is a physical impossibility and that any measure of zero is due to sensitivity limitations in current state of the art instruments and techniques.

Temperature and synthesis duration are two aspects of the reaction necessary to drive the complexation to completion. Prior to the present disclosure, the role temperature and synthesis duration play with respect to driving the metastable intermediates to full complexes had not been appreciated. Lower temperatures and shorter synthesis times result in low measurable free Gd3+ ion, but also result in a large number of unstable metastable intermediates. Past reliance on free gadolinium tests or free DOTA to determine minimum synthesis duration and temperature guarantees the presence of metastable intermediates that are unstable.

In examples, the synthesis methods for producing aqueous or dry MRI contrast agents include a delayed addition a base like meglumine, typically used in adjusting the pH of the contrast agent to physiologic levels. The pH of the human body ranges between 7.35 to 7.45, with the average at 7.40. It has been found that adding the base early can interfere with the complexation of Gd3+ with DOTA, resulting in intermediate metastable formation that is indistinguishable from fully complexed Gd3+-DOTA by the traditional xylenol orange method.

In examples, the synthesis methods for producing aqueous or dry MRI contrast agent include the use of a base other than meglumine, necessary for adjusting the pH of the contrast agent to physiologic levels. It has been found that adding a simpler molecular base prior to addition of meglumine or without addition of meglumine, where the primary complex is Gd3+-DOTA with a base other than meglumine.

The macrocyclic amines tend to be more basic than the amines in a linear structure. For this reason, addition of the basic buffer (meglumine) if added before complete complexation can further destabilize the metastable intermediate forms. This is also a novel observation of the applicants not appreciated in the art. Delay of meglumine addition until after verification of full complexification is critical to obtaining a stable GCA. In the literature, the base buffer is generally added with the uncomplexed gadolinium and ligand or before complete complexation.

Alternatively, the initial correction of the Gd3+-DOTA pH can be carried out with simpler bases such as NaOH. Or less basic bases such as (in order of increasing pKa values) protonated amines, water, alkynes, amines, alkanes.

There is a practice in the art of adding the meglumine during the Gd(dota)⁻ synthesis, before complete complexation, because early addition of base does catalyze the first step of metastable intermediate formation, but inhibits the second step of deprotonation to the final coordination complex. As a consequence of early addition of base, the protons left in the macrocyclic cavity's first coordination sphere are blocked from dissociation from the amine, which is required for the Gd3+ ion to be fully complexed. Thus, reaction time without base addition becomes a critical parameter required to fully form the thermodynamically stable product without metastable intermediates⁻.

In particular, DOTA is an acid with amine pendant groups active in the coordination process. Using a base that is not an amine to adjust the pH does not compete as strongly with the coordination process. The use of such bases, early in the pH adjustment process, and even during the coordination synthesis does not result in as much intermediate metastable formation. The catalytic effect of the base can be used to reduce Gd3+-DOTA synthesis time, and can be used in conjunction with a final metastable intermediate removal step, as disclosed here.

It is worth noting that a 1% presence by weight of metastable intermediates in a drug product equates to 10,000 ppm, well above the usual 10-100 ppm limit for free Gd3+.

To show these metastable intermediates readily evolve into free Gd3+, Gd-DOTA was placed in a solution of bovine serum and the amount of Gd3+ was measured.

Free Gd3+ after Exposure to Bovine Serum: Example 1 Vs Dotarem (gadoterate meglumine)

Bovine blood was obtained at a local slaughterhouse, citrated, centrifuged and serum was obtained and frozen. In tests, serum was slowly heated to body temperature and 1% Gd-DOTA by weight was added to serum and placed on rocker for 30 minutes. Ten samples were tested for each test article.

| Test Article | Baseline Free Gd3+[ppm] | Free Gd+ after serum [ppm] |
|---|---|---|
| Example (32 hrs) | 0.77 +/− 0.92 | 88 +/− 16.8 |
| Dotarem | 32 +/− 1.2 | 5179 +/− 24.7 |

*ppm was adjusted to pre-diluted level at drug concentration

The stability of Gd-ligand complexes strongly impacts toxicity. The thermodynamic stability of a complex simply describes the concentrations of all species present in solution at equilibrium. Inspection of the thermodynamic stability equation reveals that the Gibbs free energy of the equilibrium process will have a large favorable entropy term due to release of seven of the eight first coordination sphere water molecules from the Gd3+. Metastable intermediate complexes, where fewer than seven first coordination sphere water molecules are expelled are proportionally less stable.

The variability of the entropy contribution is unique to macrocyclic GCAs, and is a novel insight of the present disclosure. The present disclosure maximizes the entropic contribution which in turn minimizes the GCA toxicity.

Also, the metal ion-ligand interaction has a large electrostatic component that contributes an additional favorable enthalpy term so the overall free energy change becomes quite favorable. This electrostatic component is compromised when the base is added before full complexation. Generally, the enthalpy term is reduced by the presence of extra first coordination sphere water molecules.

In general, the Gd3+ aqua ion is blocked from forming the most stable complex with a ligand using the methods of the present art. Indeed, the testing methods commonly used in the art that are employed to assess complex safety cannot detect the presence of unstable metastable complex forms or metastable intermediates. Consequently, new testing methods capable of detecting the presence of metastable complex forms or metastable intermediates as provided by the present disclosure are needed.

In examples, the synthesis methods for producing aqueous MRI contrast agents are used to produce an aqueous Gd3+-DOTA complex using standard synthesis, or one of the improved synthesis methods disclosed here in conjunction with monitoring for metastable intermediates and with an acid precipitation method, which destabilized intermediate forms of chelation, but not fully formed complex, and then subsequent precipitation of the Gd3+ ion with an acid which forms an insoluble compound which can be removed by mechanical means, e.g., filtration.

In examples, the synthesis methods for producing aqueous MRI contrast agents are used to produce an aqueous Gd3+-DOTA complex using standard synthesis, or one of the improved synthesis methods disclosed here in conjunction with monitoring for metastable intermediates and with a resin capture method. Here, the complex is not destabilized, but relies on time to capture free Gd3+ ions as it is naturally thermodynamically formed from metastable intermediate formations. Generally, the free Gd3+ exists for a very short period of time, dependent on the environmental conditions. For example, when injected into a body, the Gd3+ can be blocked from re-complexification by transmetalization. Here a negatively charged resin is used, which principally competes with the amine DOTA, rather than the condition where metal competes. Here one prefers the formation of excess DOTA by removal of free Gd3+ from metastable intermediate forms, thus reducing the amount of metastable intermediate in the synthesis product. The resin is generally a solid, or coating on a solid form which permanently removes free Gd3+ from the drug product prior to packaging. The resulting free DOTA can be removed by a second step utilizing a positively charged resin.

In examples, the synthesis methods for producing aqueous MRI contrast agents are used to with a reversal of the resin technique to produce an aqueous MRI contrast agent, where the DOTA is removed by a positively charged resin and the free Gd3+ is quantified. Then a quantity of linear ligand, such a DTPA, is added to the synthesis product, and gently heated for up to about 3 hours to react the DTPA with the free DOTA, or until no free Gd3+ remains. The reason for this final chelation step is that linear ligands, such as DTPA, do not form metastable intermediate forms. The reaction product of mixed Gd3+-DOTA and Gd3+-DTPA is a fully complexed contrast agent.

In examples, the synthesis methods for producing dry MRI contrast agents are used to produce a dry Gd3+-DOTA complex using standard synthesis, or one of the improved synthesis methods disclosed here in conjunction with monitoring for metastable intermediates and with an acid precipitation method, which destabilized metastable intermediate forms of chelation, but not fully formed complex, and then subsequent precipitation of the Gd3+ ion with an acid which forms an insoluble compound which can be removed by mechanical means, e.g., filtration.

In examples, the synthesis methods for producing dry MRI contrast agents are used to produce a dry Gd3+-DOTA complex using standard synthesis, or one of the improved synthesis methods disclosed here in conjunction with monitoring for metastable intermediates and with a resin capture method. Here, the complex is not destabilized, but relies on time to capture free Gd3+ ions as it is naturally thermodynamically formed from metastable intermediate formations. Generally, the free Gd3+ exists for a very short period of time, dependent on the environmental conditions. For example, when injected into a body, the Gd3+ can be blocked from re-complexification by transmetalization. Here a negatively charged resin is used, which principally competes with the amine DOTA, rather than the condition where metal competes. Here one prefers the formation of excess DOTA by removal of free Gd3+ from metastable intermediate forms, thus reducing the amount of metastable intermediate in the synthesis product. The resin is generally a solid, or coating on a solid form which permanently removes free Gd3+ from the drug product prior to packaging. The resulting free DOTA can be removed by a second step utilizing a positively charged resin.

In examples, the synthesis methods for producing dry MRI contrast agents are used to with a reversal of the resin technique to produce an dry MRI contrast agent, where the DOTA is removed by a positively charged resin and the free Gd3+ is quantified. Then a quantity of linear ligand, such a DTPA, is added to the synthesis product, and gently heated for up to about 3 hours to react the DTPA with the free DOTA, or until no free Gd3+ remains. The reason for this final chelation step is that linear ligands, such as DTPA, do not form metastable intermediate forms. The reaction product of mixed Gd3+-DOTA and Gd3+-DTPA is a fully complexed contrast agent.

Examples according to the present disclosure can be used to build a macrocyclic cage structure around the DOTA. The cage is formed by starting with an amine base-structure of cyclen to which four arms of carboxylic acid are added. The arms can be added in sequence, one at a time. Adding one or two carboxylic acid arms is sufficient to attract the Gd3+, which is not sterically hindered, and readily complexes fully with Gd3+. Then the cage is completed around the capture Gd3+ ion by adding additional carboxylic acid arms until the complexation is complete.

Turning now to the market need, proof that the standard art does not create macrocyclic GCAs with maximum stability, i.e., contain metastable intermediates, can be found by comparing the theoretical expected free gadolinium using the rate equation to the actual measured values of commercial products stored in bottles. One should recognize the primary destabilizing factor is the presence of calcium ion when injected into the bloodstream. The actual instability is likely many orders greater than the measured free gadolinium in the bottle. For example, the theoretical free gadolinium based on the rate equation for Gd-DOTA is 69 Gd3+ ions in 100 ml of GCA product, whereas the in-bottle measured value is on the order of $10^{13}$ Gd3+ ions in 100 ml of GCA product.

The difference can be explained in terms of the stability equation. The stability constants used in the equation are the values for fully complexed GCA. If one were to use the stability constants for the metastable forms, one would get far more Gd3+ ions theoretically. As few as 10 ppm metastable forms explains the discrepancy between measured and theoretical free gadolinium ion content.

The theoretical calculation contains assumptions about how many protonation constants to include for a given ligand. Nevertheless, drug manufacturers rely on this equation to assess a particular GCA's toxicity. The stability equation is likely a good relative measure for comparing the safety of linear GCAs because linear complexes do not have metastable intermediate forms. But the reliability of this relative measure breaks down for incompletely complex macrocyclic GCAs.

Even though linear complexes with gadolinium do not readily form metastable states, the linear complexes are dynamically less stable than the macrocyclic forms. Considering all the stability variables, the macrocyclic complexes yield less free gadolinium upon injection if the metastable intermediate complexes are driven to full chelation during synthesis of the drug product.

The Gd-DOTA complex is particularly susceptible to metastable intermediate complex formation due to the strong basicity of the donor groups of DOTA. Basicity determines the affinity for protons, and positively charged ions such as Gd3+. When the Gd-DOTA GCA is fully complexed it is entirely deprotonated. However, at physiological pH values, the ligand will be partially protonated. Because DOTA is a strongly basic ligand, there is strong competition for protons at pH 7.4. The basicity which gives a higher stability for the fully complexed form, also promotes metastable intermediate formation during synthesis and liberation of free ions in the body.

Experimentally, the stability was found to be 7 orders of magnitude lower for Gd-DOTA at pH 7.4. Ironically, Gd-DTPA has a more favorable binding constant than does Gd-DOTA at pH 7.4. For less basic ligands like Gd-DTPA- BMA and DOTA-(gly)4, the experimental values are closer to the theoretical thermodynamic stability constant because there is less competition from available protons at pH 7.4.

One can expect a macrocyclic GCA with metastable intermediate forms will release in the body far more Gd3+ ion than fully complexed macrocyclic GCA. In biological media there are competitors more active than protons. For instance endogenous ions like zinc, copper, and iron form very stable complexes with these ligands. Gadolinium also has a high affinity for phosphate, citrate, and carbonate ions and will bind to proteins like serum albumin.

There is a belief in chemistry which states that in microscopically reversible states, such as Gd3+ complexes, the mechanism in one direction is exactly the reverse of the mechanism in the reverse direction. One expects the rate of complex formation should approximate the rate of complex dissociation.

The most important chemical feature that determines the toxicity of Gd-complexes is the rate of dissociation of the complex in vivo. It follows, a short synthesis time equates with a complex with a fast dissociation rate, within 30 minutes or prior to clearance from the kidney of a patient. The reduction of the synthesis time based on a free gadolinium test practically guarantees the formation of metastable intermediates which are inherently unstable, and thus are quick to dissociate. This increases the probability of transmetallation, which blocks the gd3+ ion from re-complexing with the ligand, and increases the amount of free Gd3+ ion in the body.

To show that metastable intermediate forms readily free Gd3+ in the presence of zinc, comparison was made to Examples 1A and 1B (low intermediate) and a commercial Gd-DOTA.

Transmetallation

10% by weight ZnCl solution was used to support the serum results, arguing that Zn substitution of Gd in the chelate quantifies the stability of the Gd-DOTA in much the same way that metals in serum block Gd3+ recombination with the chelate, but with more precision, since the contents of bovine serum is variable among mammals.

| GBCA | Specification Limit | In Vial | In Serum | Transmetallation |
|---|---|---|---|---|
| Example (32 hrs) | 10 | 0.77 +/− 0.92 | 2.9 +/− 0.8 | 88 +/− 16.8 |
| Dotarem | 127 | 32 +/− 1.2 | 1204 +/− 3.9 | 5179 +/− 24.7 |
| Magnevist | No Spec | 1274 +/− 5.9 | N/A | N/A |

It is important to match the elimination time in the body to the dissociation time of the chelate. Elimination time in the body is less than 2 hours, which is comparable to the complete complex formation time. Note, the complex must dissociate many times before the Gd3+ ion is replaced by a body constituent. The reason for this is that the time between dissociation and reassociation is short, and the gadolinium does not travel far from the ligand.

The present disclosure has empirically determined that synthesis time must be longer than the elimination time by at least a factor of 3, depending on the ligand. The reason for this factor is that the Gd3+ ion and ligand must first come in close proximity and maintain that proximity for the chelation time, hence the time to close approach must be added to the chelation time. One also must factor in the fact that the probability of close approach decreases as ligand is consumed. Hence, the usual synthesis time of 3 to 6 hours is grossly inadequate.

While wishing not to be bound to theory, the following encapsulates the motivation for the innovations presented in this application. Complexation of a lanthanide ion M by a polyaza polycarboxylic ligand L can take place in two ways. One reaction path comprises Equations (1) and (2) and the other path comprises Equations (1) and (3). The reaction paths involve metastable intermediate complexes (ML)* and final fully complexed form ML given by $$M+L \rightarrow (ML)^* \qquad \text{Equation (1)}$$

$$(ML)^* \rightarrow ML \qquad \text{Equation (2)}$$

$$M+L \rightarrow ML \qquad \text{Equation (3)}$$

It is important to appreciate that there are many metastable intermediate complex forms (ML)*, some of which participate in reaction pathway A given by Equations (1) and (2), and others participate in reaction pathway B given by Equations (1) and (3).

Note, the metastable intermediate species created in pathway B are unable to evolve into the final chelate ML. It is preferable to bias the synthesis to pathway A to avoid the formation of persistent metastable intermediates that must be removed. Therefore, it is desirable to employ methods which can eliminate the persistent metastable intermediates because there is no way to block pathway B completely.

Even when pathway A occurs predominantly, early termination of synthesis prevents the process given by equation (2) to convert all the metastable intermediates to the fully chelated form.

Considering pathway A, three series of successive complexes are characterized by 1) the immediate $[LnH_n(dota)]^{(n-1)+**}$, 2) the metastable $[LnH_n(dota)]^{(n-1)+*}$, and 3) fully complexed $Ln(dota)^-$ complex, where $0 \leq n \leq 2$ is the number of protons bonded to the ligand. The complexation mechanism involves three steps.

The $[LnH_n(dota)]^{(n-1)+**}$ complexes are rapidly formed, and are responsible for the premature "no free Gd3+ ion" result obtained by the improved xylenol orange titration according to the present disclosure. This metastable intermediate has the lanthanide bound to four oxygen atoms of the carboxylate groups and to five water molecules. Subsequent heat moves the lanthanide into the macrocycle cavity, two new bonds are formed with two nitrogen atoms diametrically opposed in the tetraaza cycle and only three water molecules remain bound to the lanthanide in the metastable $[LnH_n(dota)]^{(n-1)+*}$ $(0 \leq n \leq 2)$ complexes.

Further heating generates a concerted rearrangement which leads to the formation of thermodynamically stable $[Ln(dota)]^-$ complexes in which the lanthanide is bound to four nitrogen atoms, four carboxylate oxygen atoms, and one water molecule.

Figure 4:
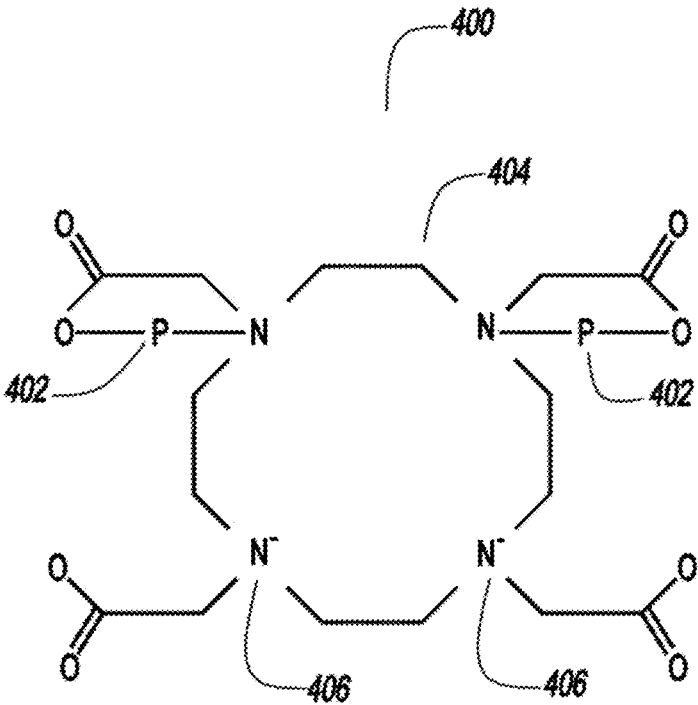
FIG. 4 shows a hydrated ligand $H_2DOTA^{2-}$.

The energetically favored free ligand structures are $H_6DOTA^{2+}$ and $H_2DOTA^{2-}$. Referring to FIG. 4, the hydrate ligand $H_2DOTA^{2-}$ 400 comprises two protons 402 and DOTA ligand 404. The ligand has a total charge −2 given by the two amine nitrogens 406.

Both structures have very similar backbone conformations, i.e., all four carboxymethyl groups point to the same direction relative to the plane formed by the four nitrogen atoms of the macrocyclic ring and maintain a syn configuration. The coordinated DOTA ligand structure is similar to that of the free form and, therefore, is preorganized for complexation.

Therefore, it is reasonable to expect pathway A to predominate with the formation of the metastable $[Gd-H_2(dota)]^+$ with the four carboxylates in the syn configuration, it probably means that its formation requires ligand rearrangement. This is consistent with the fact that the preorganized $H_2DOTA$ with the four carboxylate arms pointing to the same side forms a more stable metastable intermediate.

Figure 5:
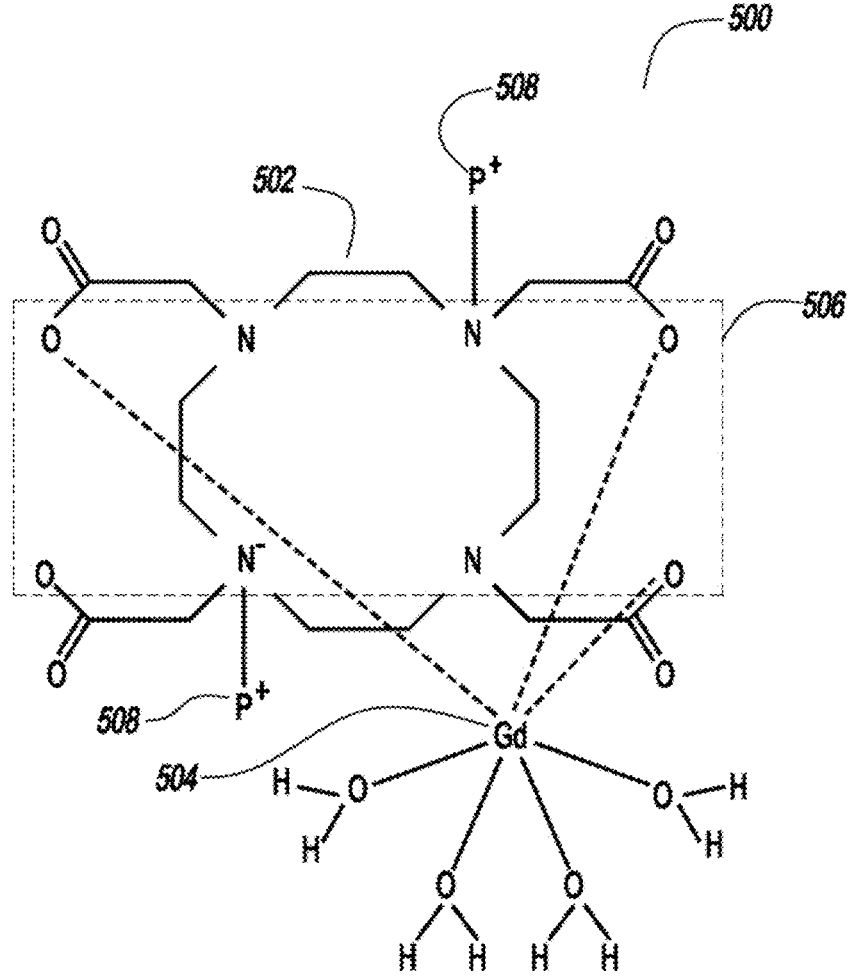
FIG. 5 shows a metastable intermediate complex $[Gd-H_2(DOTA)]^+$.

Referring to FIG. 5, the metastable $[Gd-H_2(dota)]^+$ 500 comprises ligand 502 and Gd3+ ion 504. Note the Gd+ ion 504 is outside the first coordination sphere 506. The two protons 508 must be dissociated in order for the final coordinate complex to be obtained.

The long lived $[Gd-H_2(dota)]^+$ metastable has protons at two ring nitrogen atoms trans to each other. It does not have the Gd3+ ion in the cage determined by the four ring nitrogen and four acetate oxygen atoms (C=O); rather it is coordinated only by four acetate oxygen atoms on the side away from the plane of the macrocyclic ring because of the repulsion between Gd3+ ion and the ring protons. One expects $[Gd-H_2(dota)]^+$ to be in equilibrium with $[Gd-H(dota)]$ because these two species have conformally similar structures.

In the final rate determining step, the metal ion (Gd3+) enters into the fully coordinated complex simultaneously with a thermodynamically driven deprotonation of the $[Gd-H(dota)]$ or $[Gd-H_2(dota)]^+$ metastables.

On the other hand, it is also possible the primary metastable leading to the final complex is the singly protonated GdH(dota) or triacetate derivatives of DOTA with the proton on a ring nitrogen. This metastable intermediate would have Gd3+ coordinated to at least one nitrogen in addition to the three carboxylate oxygens (C—O).

It is tempting to think the path to full complexation is just a matter of stripping off water molecules from the metastable intermediate complex. However, there is also considerable conformational change. For example, it is well-known that there are two isomers of the final complex $Gd(dota)^-$ that are observed in solution and in the crystalline form.

The major isomer M has the regular antiprism geometry and the minor isomer m has the inverted antiprism geometry, both with $C_4$ symmetry. These isomers differ in the orientation (helicity) of the carboxylate arms but have the same conformation of the tetraaza cycles. The energy difference between M and m is a few kilocalories per mole, but the barrier of interconversion from M to m is quite high. For example, in the case of Gd(dota)-complex, M is more stable than m by 4.3 kcal/mol, and the experimental barrier of interconversion from m to M is 22 kcal/mol.

From an energy barrier point of view, the final deprotonation is the rate limiting step. The energy barrier amounts to a proton transfer from NH to COO. The proton on the ring nitrogen is located inside the cage and is not accessible to outside base ($OH^-$). To expose the proton to the outside base, the cage structure must open to form 3- or 2-coordinate conformations. The energy cost is considerable. This high energy barrier for exposing the proton is consistent with the rate determining step being removal of the proton, and explains the unusually slow formation of $Gd(dota)^-$ complex and the existence of unusually stable metastable intermediate.

The mechanism of proton removal from the metastable intermediates and the energy barrier of this deprotonation process remain open questions. Two possible pathways for deprotonation of the metastable intermediates are: 1) insertion hydroxide into the cage, and 2) nitrogen inversion.

Here is proposed a novel thermodynamic mechanism which informs the method of the present disclosure. In the practice of the present disclosure, the proton is transferred from the ring nitrogen to the carboxylate oxygen by thermalization of the proton. The Gd3+ moves toward the ring in the spontaneous and concerted manner to form the octadentate coordination complex. The proton attached to the carboxylate group will be removed very fast by outside hydroxyl groups to form the final $Gd(dota)^-$ complex.

The energy barrier is lower than the energy cost needed to expose the ring proton by changing the conformation. Once the proton transfer occurs to form Gd(dota-H) (at moderate energy cost), the formation of the final $Gd(dota)^-$ complex is quite favorable because there is little conformational change required in the DOTA.

Deprotonation involves moving the proton from the inner (first) coordination sphere to the second coordination sphere.

While the loss of the proton enables the formation of the final $Gd(dota)^-$ complex, the most stable form of all the complexes, ironically the association of the Gd3+ ion to the DOTA likely decreases the metastable intermediate stability. For example, the replacement of one negatively charged carboxylate group of DOTA with a neutral amide group is known to significantly reduce the overall affinity of the ligand for lanthanide Ln3+ ions. Moving the proton from the inner nitrogen atom to the outer negatively charged carboxylate group destabilizes the complex transiently until the final complex is formed.

The enabling insight is that the minimum energy complex is the $Gd(dota)^-$ complex. The path to this stable complex involves a random sequence of metastable intermediate formations, some of which are sufficiently unstable to randomly move away from the desired final $Gd(dota)^-$ form, but given enough time, there is only one final state.

It is the instability of the metastable intermediates that allows Path B metastable intermediates to be transformed into Path A metastable intermediates. Time, temperature and proper detection are critical in obtaining a drug product of ultra-low free gadolinium potential. One refers to free gadolinium potential because these metastable intermediates are not free gadolinium, but they readily destabilize in seconds in vivo generating free Gd3+ ion, whereas the $Gd(dota)^-$ complex takes hours to dissociate in vivo. The dissociation time is comparable to the elimination time in the body.

Consequently, the presence of free gadolinium in a GCA outside the body (in the bottle) is indicative of the presence of metastable intermediates. While metastable intermediates have a low probability to dissociate into Gd3+ in the bottle, the $Gd(dota)^-$ complex has practically a zero probability to dissociate in the bottle. If the theoretical calculations are to serve as a guide, then the free Gd3+ concentration in the bottle should be well below 1 ppb, whereas free Gd3+ in commercial macrocyclic GCAs is measured over 127 and 385 ppm.

Methods to Quantify Metastable States

Laser excitation spectra of the transition of F→D electrons of Gd3+ in the presence of ligands can be used to quantify complexation metastable intermediates and final product. It is known laser excitation at 577-581 nm, emission at 614 nm, is useful in detecting the $^5D_0 \rightarrow {}^7F_2$ transition.

During the process of complexation, the initial association of Gd3+ with DOTA and the final formation of Gd(dota) result in different ligand coordination fields and therefore different excitation spectra. The complexation reaction between Gd3+ and DOTA involves the following three steps. The first step is a fast equilibrium; the second and/or the third deprotonation reaction is considered rate determining. Good excitation spectra can be obtained from 0.2 mM Gd3+(dota) solution at pH 6.10. To verify stability, the excitation spectra of a 0.2 mM Gd3+(dota) solution (pH 6.10) prepared and stored for 200 h and a solution freshly prepared by titrating a an acidic 0.2 mM Gd3+(dota) solution with $(CH_3)_4NOH$ to pH 9.90 were compared. If the two spectra are the same, the reaction product is stable.

A simple in-line test to evaluate how quickly Gd3+ is released from any chelated form is simply to add the complex to strong acid (0.1 M HCl) and measure the appearance of Gd3+ with time. The method can be modified by the addition of calcium or zinc ion, or the use of a synthetic blood serum preparation.

The relative kinetic stability of multiple runs of GCA batches is to expose the GCA to a solution containing phosphate anions at physiological pH. Even chelates with very high thermodynamic stability constants will equilibrate to form some free chelate and non-chelated gadolinium. Since gadolinium phosphate is insoluble, any non-chelated gadolinium will precipitate as insoluble gadolinium phosphate.

The detection system is to react according to Le Chatelier's Principle to establish a new equilibrium to replenish the "free gadolinium" until the phosphate anions are almost all precipitated from the solution. The rate at which this happens is determined by the rate of dissociation of Gd3+ from each metastable intermediate complex. Metastable intermediate complexes will have relatively high thermodynamic instability and a relatively fast rate of dissociation.

Example 1A: Method of Forming Aqueous Metastable-Free Gd-DOTA Synthesis

Preparation of DOTA Solution
1. Heat reactor to 25-30° C.
2. Charge water with DOTA
3. Begin stirring (stir unless otherwise indicated, nominal rate 300 rpm)
4. Charge 10% of the DOTA
5. Stir until uniformly distributed in the water
6. If all the DOTA is charged, then go to step 8
7. Go to step 4
8. Stir 10 min Preparation of Gadolinium: DOTA Complex
9. Charge 25% by weight of the Gadolinium oxide
10. Stir until uniformly distributed
11. If all the Gadolinium oxide is charged then go to step 13
12. Go to step 9
13. Stir 10 min
14. Raise temperature to 95+/−2° C.
15. Stir 3 hrs.
16. Check clarity
17. If not clear continue for 1 hr, go to step 16 (this step took about 12 hours)
18. If clear, continue 1 hr and then cool to 40-45° C.
19. If precipitate forms, heat to 95+/−2° C. and stir for 1 hr, go to step 16

Verify Gd-Dota is Free of Metastable Intermediates
20. A standard metastable-free Gd-DOTA reference solution is obtained by taking 5 ml of reactant obtained from steps 1-19 and diluting to a 0.2 mM Gd-DOTA solution. One measures the metastable intermediate content after synthesis for 5, 10, 15, 20, 25, 30, and 35 hours, or until the concentration of the metastable intermediate asymptotes as close to zero as possible.
21. The metastable intermediate content is measured by placing a 5 ml Gd-DOTA solution titrated with meglumine to pH 6.10 in a square 10 ml quartz vessel. The output from a copper vapor laser tuned to 578.2 nm (Oxford Lasers, Didcot, United Kingdom) is directed through the reactant and the excitation spectrum obtained at 578.2 nm. Baseline is established by directing the laser through the quartz vessel filled with distilled water. A graph of excitation intensity (measured in millivolts) vs reaction time is plotted, and the reference solution obtained after the slope of this plot is less than 0.01 or the absorption intensity does not change by more than 1% between 5 hour reaction intervals.
22. The stability of the reference solution can be verified by checking that the excitation spectra of a 0.2 mM Gd-DOTA solution (pH 6.10) does not change after storing for 200 h at 20° C.

Once the reference solution is prepared, then product runs can be indexed against this standard.
23. An improvement over earlier methods involves in-line or batch sample monitoring of metastable intermediate presence. For example, the monitoring can be by Fourier Transform Infrared Spectroscopy, High Performance Liquid Chromatography, Ultra High Performance Liquid Chromatography, or Trans-metalation reaction. The reactant can be titrated with a strong acid (0.1 M HCl) and the free Gd3+ ion quantified by the improved xylenol orange titration according to the present disclosure. The metastable intermediate will release free Gd3+ more quickly than fully complexed Gd-DOTA. The presence of multiple metastable intermediate forms can be detected by dynamic titration over the span of an hour or more, and calculating the Gd3+ ion as a function of time.
24. In addition, the relative kinetic stability of a Gd-DOTA complex is accessed by exposing the solution to phosphate anions at physiological pH. Even chelates with very high thermodynamic stability constants will equilibrate to form some free chelate and non-chelated gadolinium. Since gadolinium phosphate is insoluble, any non-chelated gadolinium will precipitate as insoluble gadolinium phosphate, and the free Gd3+ ion can be quantified by weighing the precipitate.

Verify Complex Formation
25. Verify absence of free gadolinium using Xylenol orange
26. If free gadolinium detected, add X DOTA, raise temperature to 95+1-2° C., stir for 1 hr and proceed to step 16
27. If not, proceed to step 23

Preparation of Gadoteric Acid Meglumine Solution
28. Add 90% of the meglumine at 40-45° C.
29. Sir 10 minutes
30. Measure pH—in-line probe calibrated to 25° C. (USP)
31. If pH is >7.5, discard
32. If pH is between 7.0 and 7.5, then go to step 29
33. If pH<than 7.0, add 2% of the Meglumine, go to step 24
34. Stir for 1 hr at 40-45° C.
35. Check solution is clear, if yes proceed to 31, if not repeat 29

Gadoteric Acid Meglumine Solution Filtration
36. Cool the solution to 20-25° C.
37. Filter the solution using the carbon filter
38. Rinse the reactor with 20-25° C. water using ¼ V
39. Pass rinse through the filter
40. Repeat rinse steps 33 & 34 for a total of 2 rinses
41. Place filtrate and rinses back in reactor
42. Stir at 25-30° C. for 10 min 43. Measure Free DOTA by HPLC 44. If Free DOTA is 0.01-0.06% ww proceed to 42

45. If Free DOTA<0.01% ww, add 0.03% ww equivalent of DOTA

46. Stir for ½ hr and go to step 38

47. Measure pH—in-line probe calibrated to 25° C. (USP)

48. If pH is between 7.0 and 7.5, then go to step 45

49. If pH<7.0, add meglumine. Stir 10 min. Go to step 42.

50. Stir ½ hr.

51. Check solution is clear, if yes proceed to 47, if not repeat 45

Verify Purity

52. Measure Purity by HPLC

53. If individual impurity>0.05%, go to step 32

Final API Adjustments

54. Measure Free DOTA by HPLC

55. If Free DOTA>0.06% ww, repeat steps 32-42

56. If Free DOTA is 0.01-0.06% ww proceed to 55

57. If Free DOTA<0.01% ww, add 0.03% ww equivalent of DOTA

58. Stir ½ hr

59. Go to Step 49

60. Measure pH

61. If pH is 7.0-7.5, then go to step 53

62. If pH<7.0, add Meglumine. Stir 10 min. Go to step 55

Final API Testing

63. Perform full API testing: Gadolinium content; Meglumine Content; Assay; Water Content; Heavy Metals Free Gadolinium as a Function of Synthesis Time Using the Method of Example 1A.

Free Gadolinium was determined by using the spectrometric xylenol orange technique described in previous studies.

| Synthesis time | Free Gd [ppm] |
|---|---|
| 4 hrs | 17,467 +/− 9.4 |
| 8 hrs | 3,448 +/− 8.9 |
| 12 hrs | 803 +/− 8.1 |
| 16 hrs | 509 +/− 4.2 |
| 20 hrs | 63.6 +/− 9.7 |
| 24 hrs | 31.0 +/− 2.1 |
| 28 hrs | 1.2 +/− 0.72 |
| 32 hrs | 0.25 +/− 0.67 |

Titrated with meglumine to pH 7.0

0.77+/−0.92

Example 1 uses a solvent free methodology. The applicants have found that the use of solvents in the synthesis process contributes to chelate instability. For example, most of the solvents used in commercial synthesis of Gd-DOTA are hydrophilic, so they can replace water in the coordination sphere. When solvent replaces water in the coordination sphere, it appears the solvent is less likely to be driven from the coordination sphere than water, thus contributing to the formation of metastable intermediates.

Effect of Solvent on Intermediate Formation and Destabilization of Stable Complex At each time step, samples were mixed with 10% v-v ethanol. The ethanol was driven from the sample by evaporation (heating under vacuum) for 12 hrs. Free Gadolinium was determined by using the spectrometric xylenol orange technique described in previous studies.

| Synthesis time | Free Gd [ppm] |
|---|---|
| 4 hrs | 71,830 |
| 8 hrs | 7,044 |
| 12 hrs | 2,146 |
| 16 hrs | 957 |
| 20 hrs | 401 |
| 24 hrs | 147 |
| 28 hrs | 92 |
| 32 hrs | 56 (compare to 0.77 without solvents) |

Example 1B: Method of Forming Dry (Solid) Metastable Intermediate-Free Gd-DOTA Synthesis Option A Preparation of DOTA Solution 1. Heat reactor to 25-30° C.

2. Charge water with DOTA

3. Stir (stir unless otherwise indicated, nominal rate 300 rpm) until the solution is clear 4. Charge 10% of the DOTA 5. Stir until uniformly distributed in the water, and clear 6. If all the DOTA is charged, then go to step 8

7. Go to step 4

8. Stir 10 min

Preparation of Gadolinium: DOTA Complex

9. Charge 25% by weight of the Gadolinium oxide

10. Stir until uniformly distributed

11. If all the Gadolinium oxide is charged then go to step 13

12. Go to step 9

13. Stir 10 min

14. Raise temperature to 95+/−2° C.

15. Stir 3 hrs.

16. Check clarity

17. If not clear continue for 1 hr, go to step 16 (this step took about 12 hours)

18. If clear, continue 1 hr and then cool to 40-45° C.

19. If precipitate forms, heat to 95+/−2° C. and stir for 1 hr, go to step 16

Verify Gd-Dota is Free of Metastable Intermediates

20. A standard metastable-free Gd-DOTA reference solution is obtained by taking 5 ml of reactant obtained from steps 1-19 and diluting to a 0.2 mM Gd-DOTA solution. One measures the metastable intermediate content after synthesis for 5, 10, 15, 20, 25, 30, and 35 hours, or until the concentration of the metastable intermediate asymptotes as close to zero as possible.

21. The metastable intermediate content is measured by placing a 5 ml Gd-DOTA solution titrated with meglumine to pH 6.10 in a square 10 ml quartz vessel. The output from a copper vapor laser tuned to 578.2 nm (Oxford Lasers, Didcot, United Kingdom) is directed through the reactant and the excitation spectrum obtained at 578.2 nm. Baseline is established by directing the laser through the quartz vessel filled with distilled water. A graph of excitation intensity (measured in millivolts) vs reaction time is plotted, and the reference solution obtained after the slope of this plot is less than 0.01 or the absorption intensity does not change by more than 1% between 5-hour reaction intervals.

22. The stability of the reference solution can be verified by checking that the excitation spectra of a 0.2 mM Gd-DOTA solution (pH 6.10) does not change after storing for 200 h at 20° C.

Once the reference solution is prepared, then product runs can be indexed against this standard.

23. An improvement over earlier methods involves in-line or batch sample monitoring of metastable intermediate presence. For example, the monitoring can be by Fourier Transform Infrared Spectroscopy, High Performance Liquid Chromatography, Ultra High Performance Liquid Chromatography, or Trans-metalation reaction. The reactant can be titrated with a strong acid (0.1 M HCl) and the free Gd3+ ion quantified the improved xylenol orange titration. The metastable intermediate will release free Gd3+ more quickly than fully complexed Gd-DOTA. The presence of multiple metastable intermediate forms can be detected by dynamic titration over the span of an hour or more, and calculating the Gd3+ ion as a function of time.

24. In addition, the relative kinetic stability of a Gd-DOTA complex is accessed by exposing the solution to phosphate anions at physiological pH. Even chelates with very high thermodynamic stability constants will equilibrate to form some free chelate and non-chelated gadolinium. Since gadolinium phosphate is insoluble, any non-chelated gadolinium will precipitate as insoluble gadolinium phosphate, and the free Gd3+ ion can be quantified by weighing the precipitate.

Verify Complex Formation

25. Verify absence of free gadolinium using Xylenol orange

26. If free gadolinium detected, add X DOTA, raise temperature to 95+1-2° C., stir for 1 hr and proceed to step 16

27. If not, proceed to step 23

Preparation of Gadoteric Acid Meglumine Solution

28. Add 90% of the meglumine at 40-45° C.

29. Sir 10 minutes

30. Measure pH—in-line probe calibrated to 25° C. (USP)

31. If pH is >7.5, discard

32. If pH is between 7.0 and 7.5, then go to step 29

33. If pH<than 7.0, add 2% of the Meglumine, go to step 24

34. Stir for 1 hr at 40-45° C.

35. Check solution is clear, if yes proceed to 31, if not repeat 29

Gadoteric Acid Meglumine Solution Filtration

36. Cool the solution to 20-25° C.

37. Filter the solution using the carbon filter

38. Rinse the reactor with 20-25° C. water using ¼ V

39. Pass rinse through the filter

40. Repeat rinse steps 33 & 34 for a total of 2 rinses

41. Place filtrate and rinses back in reactor

42. Stir at 25-30° C. for 10 min

43. Measure Free DOTA by HPLC

44. If Free DOTA is 0.01-0.06% ww proceed to 42

45. If Free DOTA<0.01% ww, add 0.03% ww equivalent of DOTA

46. Stir for ½ hr and go to step 38

47. Measure pH—in-line probe calibrated to 25° C. (USP)

48. If pH is between 7.0 and 7.5, then go to step 45

49. If pH<7.0, add meglumine. Stir 10 min. Go to step 42.

50. Stir ½ hr.

51. Check solution is clear, if yes proceed to 47, if not repeat 45

Verify Purity

52. Measure Purity by HPLC

53. If individual impurity>0.05%, go to step 32

Final API Adjustments

54. Measure Free DOTA by HPLC

55. If Free DOTA>0.06% ww, repeat steps 32-42

56. If Free DOTA is 0.01-0.06% ww proceed to 55

57. If Free DOTA<0.01% ww, add 0.03% ww equivalent of DOTA

58. Stir ½ hr

59. Go to Step 49

60. Measure pH

61. If pH is 7.0-7.5, then go to step 53

62. If pH<7.0, add Meglumine. Stir 10 min. Go to step 55

Final API Testing

63. Perform full API testing: Gadolinium content; Meglumine Content; Assay; Water Content; Heavy Metals 64. Place finished API solution in trays in a vacuum equipped oven. Other non-solvent based methods of removing the water are known in the art, e.g., a rotary desiccator. Heat oven to 95° C. at highest vacuum value until API has less than or equal to 300 ppm water, or flows freely. The dried API may require pulverization, since the dried API generally has the form of a cohesive brick.

Option B: The drying step may be applied at step 28 to obtain a dry Gd-DOTA complex prior to buffering with meglumine. Meglumine and water can be added during the packaging process.

Option C: The drying step may be applied at step 54 to obtain a dry Gd-DOTA meglumine complex prior final adjustments. Final adjustment and water can be added during the packaging process.

Free Gadolinium as a Function of Synthesis Time Using the Method of Example 1.

Free Gadolinium was determined by using the improved spectrometric xylenol orange technique described in previous studies.

| Synthesis time | Free Gd [ppm] |
| --- | --- |
| 4 hrs | 17,467 +/− 9.4 |
| 8 hrs | 3,448 +/− 8.9 |
| 12 hrs | 803 +/− 8.1 |
| 16 hrs | 509 +/− 4.2 |
| 20 hrs | 63.6 +/− 9.7 |
| 24 hrs | 31.0 +/− 2.1 |
| 28 hrs | 1.2 +/− 0.72 |
| 32 hrs | 0.25 +/− 0.67 |

Titrated with meglumine to pH 7.0

0.77+/−0.92

Example 1B also uses a solvent free methodology. The applicants have found that the use of solvents in the synthesis process contributes to chelate instability. For example, most of the solvents used in commercial synthesis of Gd-DOTA are hydrophilic, so they can replace water in the coordination sphere. When solvent replaces water in the coordination sphere, it appears the solvent is less likely to be driven from the coordination sphere than water, thus contributing to the formation of metastable intermediates.

Effect of Solvent on Intermediate Formation and Destabilization of Stable Complex At each time step, samples were mixed with 10% v-v ethanol. The ethanol was driven from the sample by evaporation (heating under vacuum) for 12 hrs. Free Gadolinium was determined by using the improved spectrometric xylenol orange technique described in previous studies.

| Synthesis time | Free Gd [ppm] |
|---|---|
| 4 hrs | 71,830 |
| 8 hrs | 7,044 |
| 12 hrs | 2,146 |
| 16 hrs | 957 |
| 20 hrs | 401 |
| 24 hrs | 147 |
| 28 hrs | 92 |
| 32 hrs | 56 (compare to 0.77 without solvents) |

Example 2A: Aqueous Metastable-Free Gd-Dota Synthesis

If it is desired to minimize the synthesis time, then the metastable intermediates can be removed after step 20 or after step 59 of Example 1A using the phosphate precipitation method.

A simple in-line test to evaluate how quickly Gd3+ is released from any chelated form is simply to add the complex to strong acid (0.1 M HCl) and measure the appearance of Gd3+ with time. The method can be modified by the addition of calcium or zinc ion, or the use of a synthetic blood serum preparation.

The relative kinetic stability of multiple runs of GCA batches is to expose the GCA to a solution containing phosphate anions at physiological pH. Even chelates with very high thermodynamic stability constants will equilibrate to form some free chelate and non-chelated gadolinium. Since gadolinium phosphate is insoluble, any non-chelated gadolinium will precipitate as insoluble gadolinium phosphate.

The detection system is to react according to Le Chatelier's Principle to establish a new equilibrium to replenish the "free gadolinium" until the phosphate anions are almost all precipitated from the solution. The rate at which this happens is determined by the rate of dissociation of Gd3+ from each metastable intermediate complex. metastable intermediate complexes will have relatively high thermodynamic instability and a relatively fast rate of dissociation.

The feasibility of acid precipitation as a method for making Gd-DOTA with low metastable intermediate forms was tested.

Ten samples were tested using the improved spectrometric xylenol orange method after 1 hr exposure to acid (0.1 M HCl), buffer to pH 7.0, and filtration of the precipitate.

12 hour Example 1A sample was used at 803 ppm Gd3+
After acid precipitation (N=5)
8.6+/−9.2 ppm Gd3+ range: 15.9 ppm Gd3+ to undetectable

Example 2B: Dry Metastable-Free Gd-Dota Synthesis

If it is desired to minimize the synthesis time, then the metastable intermediates can be removed after step 20 or after step 59 of Example 1B using the phosphate precipitation method.

A simple in-line test to evaluate how quickly Gd3+ is released from any chelated form is simply to add the complex to strong acid (0.1 M HCl) and measure the appearance of Gd3+ with time. The method can be modified by the addition of calcium or zinc ion, or the use of a synthetic blood serum preparation.

The relative kinetic stability of multiple runs of GCA batches is to expose the GCA to a solution containing phosphate anions at physiological pH. Even chelates with very high thermodynamic stability constants will equilibrate to form some free chelate and non-chelated gadolinium. Since gadolinium phosphate is insoluble, any non-chelated gadolinium will precipitate as insoluble gadolinium phosphate.

The detection system is to react according to Le Chatelier's Principle to establish a new equilibrium to replenish the "free gadolinium" until the phosphate anions are almost all precipitated from the solution. The rate at which this happens is determined by the rate of dissociation of Gd3+ from each metastable intermediate complex. Metastable intermediate complexes will have relatively high thermodynamic instability and a relatively fast rate of dissociation.

The feasibility of acid precipitation as a method for making Gd-DOTA with low metastable intermediate forms was tested.

Ten samples were tested using the improved spectrometric xylenol orange method after 1 hr exposure to acid (0.1 M HCl), buffer to pH 7.0, and filtration of the precipitate.

12 hour Example 1B sample was used at 803 ppm Gd3+
After acid precipitation (N=5)
8.6+/−9.2 ppm Gd3+ range: 15.9 ppm Gd3+ to undetectable.

Example 3: Establishing Minimum Detection Levels

The ability to measure a minimum concentration of 1 ppm Gd3+ ion depends on being able to prepare a $10^{-6}$ molar solution of Gd3+ and a 1 molar solution of Xylenol orange to an accuracy of $10^{-6}$.

The Xylenol orange titration relies on a solution color change. Since the photon source used to assess color change will not be isomorphic in wavelength, one needs to calibrate the source and detector for each of the two wavelengths quantified in the xylenol orange method (see USP Memorandum on Gadolinium Contrast Agents). The calibration is only as good as the thermal stability of the source and detector. Therefore, it will be important to put source and detector into thermal equilibrium before measurement, therefore a 1 hour baseline must be established where the calibration varies by less than 10 ppm signal.

The entire measurement setup is to be placed in a thermally controlled environmental chamber at 20° C.

For these reasons, 10 separate 1 ppm Gd(III) solutions were prepared and equilibrated to 20° C. It is not sufficient to make one solution and take 10 measurements. Each of the 10 standard solutions are to be measured a minimum of 10 times, by performing a time integration until the variability reaches the 1 ppm threshold. This is possible by the programmable algorithm interface of commercial spectrometers.

The above procedure is to be repeated for 10 ppm solution and 100 ppm. Based on naive thermodynamic considerations, it is expected the robust (standard deviation less than 10%) detection range will start at between 10 ppm and 100 ppm.

Once the robust detection range is established, then the variability in decades is to be quantified: 1000 ppm, 10,000 ppm (1%), and 100,000 ppm (10%).

Calibration Results

The concentration of a solution of Gd(III) ion is determined stoichiometrically where the concentration is given by $$\frac{[Gd(III)]}{[XO]} X 10^6 = ppm \ Gd(III)$$

[ . . . ] is the molar amount of Gd(III) or Xylenol Orange. In terms of spectral measurement $$\frac{Abs^{573}}{Abs^{573} + Abs^{433}} X 10^6 = ppm \ Gd(III)$$

Ten 1 ppm Gd(III) ion solutions were titrated to 7.0+/−0.1 pH with NaOH and the ammonia removed by vacuum. Standard deviations are the result of integration of 10 spectrometer runs, N=10.

| | 1 ppm | 10 ppm | 100 ppm | 1000 ppm | 10,000 ppm | 100,000 ppm |
|---|---|---|---|---|---|---|
| Solution 1 | 5.6 +/− 0.6 | 14.8 +/− 0.6 | 93.7 +/− 0.7 | 1009.3 +/− 0.5 | 10,006.6 +/− 0.9 | 100,005.7 +/− 0.5 |
| Solution 2 | 3.1 +/− 0.7 | 17.0 +/− 0.4 | 95.5 +/− 0.6 | 992.8 +/− 0.5 | 10,009.3 +/− 0.8 | 99,993.1 +/− 0.3 |
| Solution 3 | 2.6 +/− 0.6 | 11.5 +/− 0.9 | 102.6 +/− 0.3 | 1005.6 +/− 0.7 | 9.996.8 +/− 0.2 | 99,998.9 +/− 0.0 |
| Solution 4 | 0.1 +/− 0.2 | 8.9 +/− 0.2 | 109.2 +/− 0.0 | 1009.7 +/− 0.5 | 9,991.6 +/− 0.3 | 99,991.8 +/− 0.3 |
| Solution 5 | 1.5 +/− 0.0 | 8.5 +/− 0.9 | 97.3 +/− 0.3 | 1006.5 +/− 0.8 | 10,006.3 +/− 0.4 | 99,993.1 +/− 0.5 |
| Solution 6 | 2.3 +/− 0.4 | 5.9 +/− 0.3 | 92.8 +/− 0.1 | 1001.9 +/− 0.6 | 10,002.4 +/− 0.0 | 99,995.8 +/− 0.7 |
| Solution 7 | 6.9 +/− 0.1 | 12.7 +/− 0.2 | 97.1 +/− 0.4 | 991.4 +/− 0.3 | 9,992.2 +/− 0.0 | 99,992.9 +/− 0.6 |
| Solution 8 | 4.9 +/− 0.0 | 4.9 +/− 0.0 | 92.5 +/− 0.9 | 1003.9 +/− 0.5 | 10,009.5 +/− 0.6 | 100,000.6 +/− 0.5 |
| Solution 9 | 0.7 +/− 0.1 | 10.6 +/− 0.7 | 103.6 +/− 0.0 | 994.0 +/− 0.1 | 10,002.8 +/− 0.9 | 100,002.1 +/− 0.5 |
| Solution 10 | 1.8 +/− 0.3 | 12.9 +/− 0.3 | 94.6 +/− 0.9 | 1007.9 +/− 0.4 | 10,003.7 +/− 0.4 | 99,995.3 +/− 0.5 |
| MEAN | 3.0 +/− 2.1 | 10.8 +/− 3.6 | 97.9 +/− 5.2 | 1002.3 +/− 6.7 | 10,002.1 +/− 6.2 | 99,996.9 +/− 4.4 |

Example 4. Identification of Metastables in Incompletely Synthesized Complex Solution Using Example 1, metastable intermediate forms and free Gd3+ was quantified. 40.5 g of DOTA was suspended in 150 ml of water at a temperature of 75° C. 17.8 g of gadolinium oxide was added, and the batch was stirred at 75° C. for 2 hours. The solution that was produced was mixed with 19.5 g of meglumine and stirred at 75° C. for one hour. Then, the content of free DOTA, free gadolinium, and complex was determined, and the final content of excess free DOTA was set.

Five reactions were run, using 4.05 g of DOTA, 15 ml water, and 1.78 g of gadolinium oxide. Ten spectroscopic measurements using Xylenol orange were conducted. Here the calculation of ppm is different, where the amount of xylenol orange equals the number of theoretical drug molecules, that is for each gadolinium oxide molecule one will generate two gadolinium ions which can either complex with DOTA or remain free, accordingly [XO]=[GdO X 2]. This is the molar amount of xylenol orange added to each reaction product. One can use:

$$\frac{Abs^{573}}{Abs^{573} + Abs^{433}} X 10^6 = ppm \ Gd(III)$$

Understanding that the denominator is a constant and Abs$^{573}$ is the number of free Gd(III) ions that react with the xylenol orange. This is a conservative measure of ppm, given by the ratio of free gadolinium and total gadolinium in the reactant ($\times 10^6$). Another possible definition, which would give a higher number (less conservative) is simply comparing free gadolinium to complexed gadolinium, which would mean ppm of free gadolinium for every million complexed gadolinium. The two definitions depart significantly at free gadolinium concentrations above 1%.

| Reaction # | Free Gd(III) |
|---|---|
| Reaction 1 | 30,415.3 +/− 4.4 |
| Reaction 2 | 19,567.6 +/− 3.5 |
| Reaction 3 | 22,989.0 +/− 0.6 |
| Reaction 4 | 36,080.7 +/− 3.8 |
| Reaction 5 | 45,890.4 +/− 7.6 |
| MEAN | 30,989 +/− 9410 ppm |

Example 5. Metastables as a Function of Reaction Time

Stoichiometric ratios of gadolinium oxide were reacted with DOTA according to the procedure outlined in Example 1. Measurements were taken (N=1) to conserve volume. The final measurement was performed 5 times.

| Hours of reaction | Metastable Intermediates [ppm] | |
|---|---|---|
| 3 hours | 28,094 +/− 9.7 | N = 1 |
| 8 hours | 3,853 +/− 12.4 | N = 1 |
| 24 hours | 72 +/− 5.0 | N = 1 |
| 32 hours | 0.8 +/− 1.3 | N = 10 |

Now titrate with meglumine to pH 7.0

| 1.2 +/− 3.8 | N = 2 |
|---|---|

Example 6: Metastable-Free Gd-DOTA Synthesis

Here a metastable-free Gd-DOTA synthesis is obtained by performing a synthesis according to a shortened version of Example 1, or a more standard synthesis with possibly early meglumine addition, which yields a product synthesis containing metastable intermediates or metastable complexations. As the Gd3+ forms in the reaction product, the Gd3+ can be captured and sequestered on a negatively charged resin. For example, a polyurethane prepolymer with at least two arms functionalized with pendant amine groups.

Figure 6:
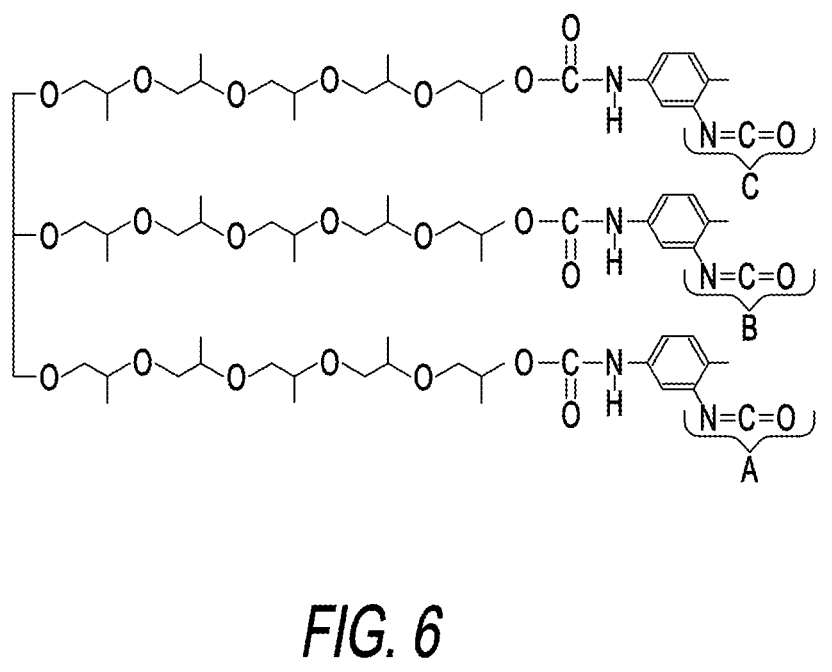

Referring to FIG. 6, a prepolymer 600 comprising 3 arms 602 each encapped with isocyanate functionality 604 is made from a poloxamer triol such as dry (<300 ppm H$_2$O) Multranol 3901 (Bayer, Morristown, NJ) containing 1 mole of hydroxyl groups is combined with toluene diisocyanate containing 2 moles of NCO groups in a glass reactor equipped with a stirrer, heating jacket and temperature sensor. The reactor is purged with dry nitrogen and the mixture stirred. The reaction volume is heated to 40° C. and allowed to react until the exotherm has subsided. Then the temperature of the reactor is increased in 5° C. increments, stopping after each increment to let the exotherm subside, until a temperature of 65 OC is reached. The reaction mixture is further reacted until 1 mole of isocyanate group is consumed. This end point can be determined by measuring the % NCO.

The prepolymer 600 can be reacted with a solid polyurethane with pendant amine groups to form a solid resin coated with prepolymer 600. The pendant amine groups will react with Gd3+ ion immobilizing the free ion on the solid polyurethane, which can easily be mechanically removed.

Feasibility of cation exchange as a method of making Gd-DOTA with low metastable intermediates Using sodium polystyrene sulfonate, rather than the polymer described above.

Example 1 sample at 2146 ppm Gd3+

Ten samples were stored at room temperature with a stoichiometric amount of sodium polystyrene sulfonate.

Samples were tested using the improved spectrometric xylenol orange method.

| After samples treated (N = 5) | |
| --- | --- |
| 685 +/− 9.4 | 24 hrs |
| 292 +/− 15.2 | 48 hrs |
| 8.9 +/− 8.5 | 96 hrs |

Example 7. Metastable-Free Gd-DOTA Synthesis

The metastable intermediate concentration is determined by Example 3, and associated methods described in the present application. A Gd-DOTA synthesis containing metastable intermediates is heated to 95° C. in the presence of a stoichiometric amount of DTPA sufficient to consume all the metastable intermediates. The presence of metastable intermediates can be measured as a function of time. The reaction is continued until a desired metastable intermediate content is obtained. Depending on the amount of free DOTA thus liberated, the free DOTA can be reacted with a positively charged resin, as is known in the art. Alternatively, the free DOTA may serve as a buffer against free Gd3+ formation, as is permitted in some drug formulations.

Feasibility of Excess DTPA as a Method of Making Gd-DOTA with Low Metastable Intermediates Make new 12 hour Example 1 sample at 2146 ppm Gd3+

Ten samples were prepared by adding stoichiometric amounts of DTPA to counter the excess Gd3+ and stored at room temperature for 24 hours.

Samples were tested using the improved spectrometric xylenol orange method.

After samples treated with DTPA (N=5)

14.8+/−11.6 range: 27.6 ppm Gd3+ to undetectable

Example 8. Metastable-Free Gd-DOTA Synthesis

Figure 7:
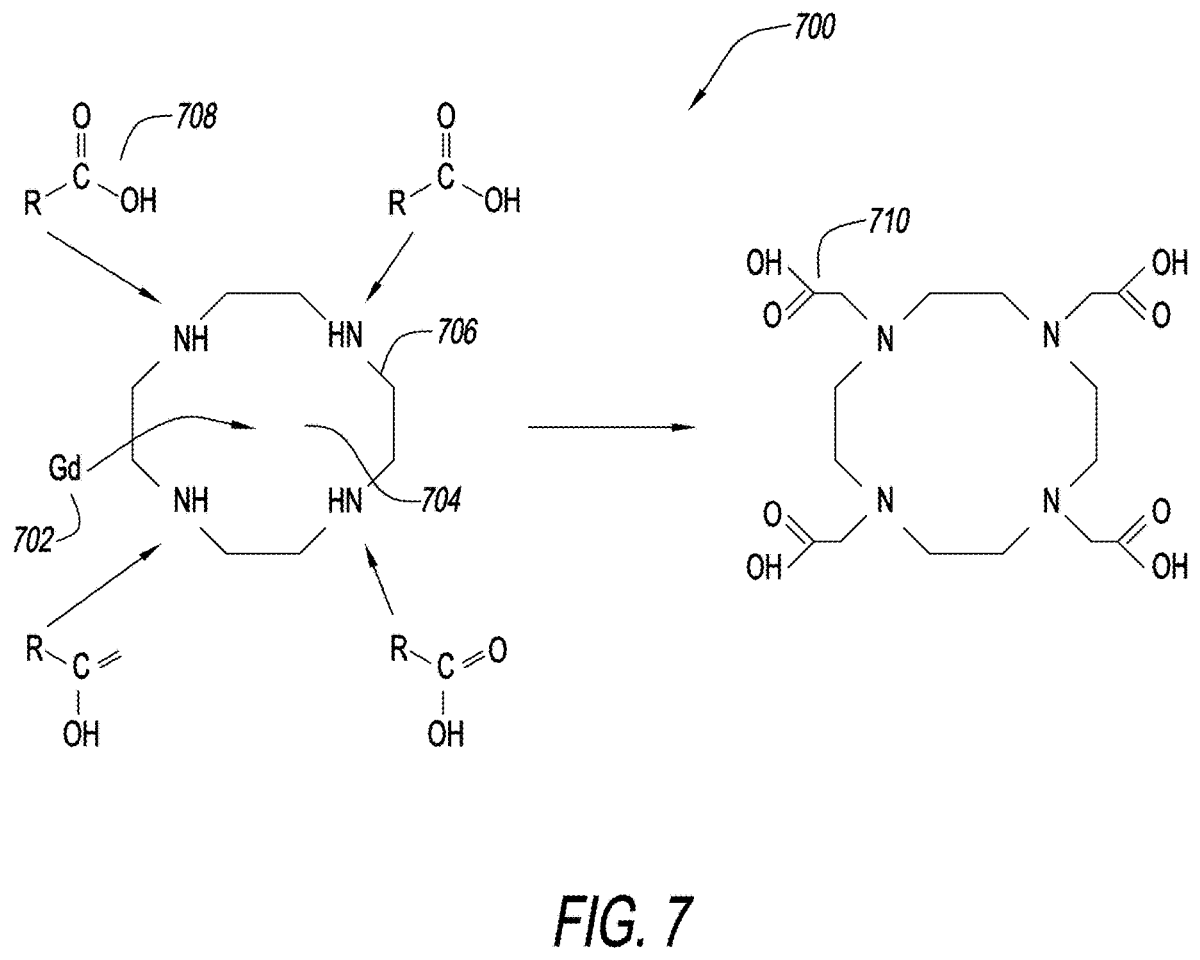

Referring to FIG. 7, Gd-DOTA 700 is formed by associating a cyclen molecule 706 and Gd3+ ion 702. When they are proximal in solution and heated, the Gd3+ is captured at location 704 of the cyclen molecule 706. Carboxylic acid arms 710 in the form of carboxylic acid 708 are added sequentially to the cyclen molecule 706. The free Gd3+ content can be measured in process to ensure complexation occurs prior to the addition of the third arm, which begins to close the cage around the Gd3+ ion.

Alternatively, referring to FIG. 7, the cyclen molecule 700 and Gd3+ ion 702 are proximal in solution. Carboxylic acid arms 704 are added sequentially to the cyclen molecule 700. The free Gd3+ content can be measured in process to ensure complexation occurs prior to the addition of the third arm, which begins to close the cage around the Gd3+ ion.

The procedure can be done in aqueous solution or in solvent. The solvent is replaced by water. In a solvent based reaction, for example, comprises dissolving 10 mg powder cyclen (cyclen 1,4,7,10-tetra-azaclylododecane) in dry THF, and measuring water content by Karl-Fischer. The result is usually given as ppm by weight, and the water mass must be subtracted from the measured cyclen mass to find mole amounts.

One mole of Cyclen weighs 172.27 g/mole. If the Cyclen contains 10,000 ppm water, then to obtain 1 mole of Cyclen one needs to take $(1+10^4/10^6) \times 172.27$ g/mole=174.0 g 1. Dissolve 0.1 mole of cyclen 1,4,7,10-tetra-azaclylodo-decane (cyclen) and 0.05 mole Gd2O3 in 100 ml of distilled water.

2. Prepare 4 portions of a sodium chloroacetate solution by filling a beaker with 0.15 moles (approximately 14.18 g) a magnetic stir at room temperature. Place a pH probe in the stirred solution, add in increments powdered NaOH until pH>13 is obtained. The reaction is moderately exothermic, so using the thermometer function on the pH meter to maintain temperature between 25-30° C.

3. Allow the sodium chloroacetate solutions to cool to 20-25° C.

4. Using a graduated column, titrate one portion of the sodium chloroacetate solution to the cyclen solution at a rate of 10 ml per minute, or at a rate sufficiently slow to keep the temperature in the 20 to 25° C. range and the temperature in the range 9.0 to 10.0 pH.

5. When the target pH range is reached, stop the sodium chloroacetate addition, place the reactant under a nitrogen blanket while stirring, and raise the reactant temperature to 80° C. at a rate not to exceed 5° C. per minute. While stirring, monitor the pH, and add sodium chloroacetate to maintain pH=9.0-10.0. The rate of titration will decrease with time.

6. At 12 hours, or when the rate of titration drops below 1 ml sodium chloroacetate per hour take a sample for HLPC.

7. Continue to stir the heated mixture until the main peak in the HPLC exceeds 95%, or when the main peak is no longer getting larger.

8. Cool to room temperature and store in glass bottle under nitrogen.

9. Obtain free Gd3+ content.

10. Repeat step 4-9 for the second portion of chloroacetate solution.

11. If free Gd3+ has reached target value then continue with steps 4-9 two more cycles until all four portions of chloroacetate solution are consumed. One can perform HPLC to verify Gd-DOTA complex is obtained.

12. If free Gd3+ has not reached target, continue heating at 95° C. until target is reached.

13. Isolate by precipitation or keep in water solution.

14. Purify with ionic resin.

Example 9 Bi-Chelate Metastable-Free Gd-DOTA Synthesis

It is possible for Gd3+ to associate with two DOTA molecules, and not have either DOTA enter fully the coordination sphere of the Gd3+. As in the case of the partially chelated Gd-DOTA complex, a DOTA-Gd-DOTA complex is not free gadolinium, but is even more unstable than the partially chelated Gd-DOTA metastable intermediate. These species are relatively easy to detect on HPLC or similar molecular weight dependent measurements. Therefore, the bi-chelate metastable intermediate form will show up as a biocompatible contaminant, and therefore regulations do not require removing the contaminant if the contaminant is below 0.05% or 500 ppm. However, 500 ppm free Gd in the body is very toxic, and two orders of magnitude above the levels achieved in the present patent.

The following procedure can be used.

Preparation of DOTA Solution
15. Heat reactor to 25-30° C.
16. Charge water with DOTA
17. Begin stirring (stir unless otherwise indicated, nominal rate 300 rpm)
18. Charge 10% of the DOTA
19. Stir until uniformly distributed in the water
20. If all the DOTA is charged, then go to step 8
21. Go to step 4
22. Stir 10 min Preparation of Gadolinium: DOTA Complex
23. Charge 25% by weight of the Gadolinium oxide
24. Stir until uniformly distributed
25. If all the Gadolinium oxide is charged then go to step 13
26. Go to step 9
27. Stir 10 min
28. Raise temperature to 95+/−2° C.
29. Stir 3 hrs.
30. Check clarity
31. If not clear continue for 1 hr, go to step 16 (this step took about 12 hours)
32. If clear, continue 1 hr and then cool to 40-45° C.
33. If precipitate forms, heat to 95+/−2° C. and stir for 1 hr, go to step 16

Verify Gd-Dota is Metastable-Free
34. A standard metastable-free Gd-DOTA reference solution is obtained by taking 5 ml of reactant obtained from steps 1-19 and diluting to a 0.2 mM Gd-DOTA solution. One measures the metastable intermediate content after synthesis for 5, 10, 15, 20, 25, 30, and 35 hours, or until the concentration of the metastable intermediate asymptotes as close to zero as possible.
35. The metastable intermediate content is measured by placing a 5 ml Gd-DOTA solution titrated with meglumine to pH 6.10 in a square 10 ml quartz vessel. The output from a copper vapor laser tuned to 578.2 nm (Oxford Lasers, Didcot, United Kingdom) is directed through the reactant and the excitation spectrum obtained at 578.2 nm. Baseline is established by directing the laser through the quartz vessel filled with distilled water. A graph of excitation intensity (measured in millivolts) vs reaction time is plotted, and the reference solution obtained after the slope of this plot is less than 0.01 or the absorption intensity does not change by more than 1% between 5 hour reaction intervals.

36. The stability of the reference solution can be verified by checking that the excitation spectra of a 0.2 mM Gd-DOTA solution (pH 6.10) does not change after storing for 200 h at 20° C.

Once the reference solution is prepared, then product runs can be indexed against this standard.

37. An improvement over earlier methods involves in-line or batch sample monitoring of metastable intermediate presence. For example, the monitoring can be by Fourier Transform Infrared Spectroscopy, High Performance Liquid Chromatography, Ultra High Performance Liquid Chromatography, or Trans-metalation reaction. The reactant can be titrated with a strong acid (0.1 M HCl) and the free Gd3+ ion quantified by the improved xylenol orange titration. The metastable intermediate will release free Gd3+ more quickly than fully complexed Gd-DOTA. The presence of multiple metastable intermediate forms can be detected by dynamic titration over the span of an hour or more, and calculating the Gd3+ ion as a function of time.

38. In addition, the relative kinetic stability of a Gd-DOTA complex is accessed by exposing the solution to phosphate anions at physiological pH. Even chelates with very high thermodynamic stability constants will equilibrate to form some free chelate and non-chelated gadolinium. Since gadolinium phosphate is insoluble, any non-chelated gadolinium will precipitate as insoluble gadolinium phosphate, and the free Gd3+ ion can be quantified by weighing the precipitate.

39. Verify absence of DOTA-Gd-DOTA complex by running HPLC, looking for peaks corresponding to the molecular weight of this complex. If detected, the amount of the DOTA-Gd-DOTA contaminant is to be calculated using the Gd-DOTA peak and comparing integrated area under the respective peaks. Then a suitable amount of gadolinium oxide is to be added to take up the extra DOTA, and the reaction is to be continued at 95 degrees C. for 3 hrs, and then steps 20-25 are to be repeated until the amount of metastable intermediate species is in acceptable ranges.

Then Example 1B is to be resumed at step 25.

Example 10. Faster Synthesis with a Salt of Gadolinium

Gadolinium oxide is reluctant to go into solution. As described in Example 1, it is important that all the gadolinium oxide go into solution and the solution be clear before introducing the DOTA. Gadolinium oxide will go into solution faster if the water contains positive ions from a gadolinium salt, for example gadolinium chloride. The small amount of chloride ion introduced my this method can be removed by ionic resin later in the API preparation process, or reacted with sodium to yield sodium chloride at levels acceptable for injection. The procedure is as in Example 1, except the first step is to dissolve 10 mg of gadolinium chloride in the water before adding the gadolinium oxide. Depending on the amount of time one wishes to reduce the time required to form Gd-DOTA complex, more gadolinium chloride can be added during the Gd-DOTA synthesis, ore more can be added initially.

Example 11. Freezing Out Coordination Water

A Gd-DOTA synthesis should be performed as in Example 1B. After verifying the free Gd3+ is within a first synthesis target level but not below a drug product target level, then the aqueous composition can be slowly chilled in a vibration-free environment so that the aqueous Gd-DOTA reaches its freezing point without solidification. Then a sudden mechanical disturbance of the solution volume can instantly convert the liquid volume into a solid. The resulting water expansion will preferentially push water out of the coordination sphere. Then subsequent slow reheating will allow the partially chelated gadolinium in a metastable intermediate complex to form a more fully complex form, thus removing a significant fraction of the metastable intermediate complex.

Example 12 pH Controlled Synthesis

Here, Example 1A is modified by the addition of gadolinim oxide in its entirety at first and immediately after the introduction of the DOTA, and this procedure is used to produce batch A of Gd-DOTA. Batch B is produced using the following modified procedure.
Preparation of Gd-DOTA Solution 1. Heat reactor to 95° C.
2. Charge water with all of gadolinium oxide
3. Stir (stir unless otherwise indicated, nominal rate 300 rpm) until the solution is clear
4. Add sufficient DOTA to obtain a pH of 4
5. When pH is >5 charge sufficient DOTA to reach pH of 4
6. Stir until uniformly distributed in the water, and clear
7. If pH<4, then go to step 9
8. Go to step 4
9. Divide remaining portion of DOTA into 5 parts
10. Add 1 part of remaining DOTA
11. Stir until uniformly distributed in the water, and clear
12. If DOTA remains to be added go to step 10
13. Continue to cook for a total of 12 hours Results

| Synthesis time | Example 1 (Free Gd [ppm]) | Batch A | Batch B (Example 12) |
|---|---|---|---|
| 4 hrs | 17,467 +/− 9.4 | 15,036 +/− 12.8 | 19,276 +/− 6.3 |
| 8 hrs | 3,448 +/− 8.9 | 4,947 +/− 9.9 | 2,793 +/− 7.1 |
| 12 hrs | 803 +/− 8.1 | 1,792 +/− 10.5 | 377 +/− 5.2 |

As used herein, the terms "a" and "an" mean "one or more" unless specifically indicated otherwise.

As used herein, the term "comprising" means "including, but not limited to; the term "consisting essentially of" means that the method, structure, or composition includes steps or components specifically recited and may also include those that do not materially affect the basic novel features or characteristics of the method, structure, or composition; and the term "consisting of" means that the method, structure, or composition includes only those steps or components specifically recited.

As used herein, the term "about" is used to provide flexibility to a numerical range endpoint by providing that a given value can be "a little above" or "a little below" the endpoint as is customary in the art. Further, where a numerical range is provided, the range is intended to include any and all numbers within the numerical range, including the end points of the range.

While the present disclosure has been described with reference to one or more exemplary embodiments, it will be understood by those skilled in the art, that various changes can be made, and equivalents can be substituted for elements thereof without departing from the scope of the present disclosure. In addition, many modifications can be made to adapt a particular situation or material to the teachings of the present disclosure without departing from the scope thereof. Therefore, it is intended that the present disclosure will not be limited to the particular embodiments disclosed herein, but that the disclosure will include all aspects falling within the scope of a fair reading of appended claims.

What is claimed is:

1. A method of making a lanthanide series contrast agent, wherein the lanthanide series contrast agent comprises at least one atom of lanthanide series metal and at least one macrocyclic chelate, said method comprising:
    (a) reacting a macrocyclic chelate with a lanthanide series metal oxide in water at a temperature and reaction time sufficient to provide a lanthanide series metal ion: macrocyclic chelate complex, wherein the macrocyclic chelate is 1,4,7,10-Tetraazacyclododecane-1,4,7,10-tetraacetic acid (DOTA) and has <10 ppm impurities containing a cyclen ring, and wherein the lanthanide series metal is gadolinium;
    (b) monitoring the reaction of the macrocyclic chelate with the lanthanide series metal oxide to determine a content of metastable intermediates, wherein the metastable intermediates are partially chelated complexes of the lanthanide series metal ion:macrocyclic chelate complex;
    (c) returning to (a) if the content of metastable intermediates determined by (b) exceeds 500 parts per million relative to a total amount of the lanthanide series metal ion:macrocyclic chelate complexes present; and
    (d) reacting the lanthanide series metal ion:macrocyclic chelate complex with a base at a temperature and reaction time sufficient to provide a complex of lanthanide series metal ion, macrocyclic chelate, and base in an aqueous formulation, wherein the aqueous formulation comprises less than about 500 parts per million of metastable intermediates relative to a total amount of the lanthanide series metal ion:macrocyclic chelate complexes present in the aqueous formulation, wherein the method is performed without use of solvents.

2. The method of claim 1, wherein the monitoring is performed in situ.

3. The method of claim 1, further comprising: after (d),
    (e) monitoring the reaction of the lanthanide series metal ion:macrocyclic chelate complex with a base to determine the content of metastable intermediates and
    (f) returning to (d) if a content of metastable intermediates determined by (e) exceeds 500 parts per million.

4. The method of claim 1, wherein the (c) returning to (a) is performed if the content of metastable intermediates determined by (b) exceeds 100 parts per million.

5. The method of claim 1, wherein the (f) returning to (d) is performed if the content of metastable intermediates determined by (e) exceeds 100 parts per million.

6. The method of claim 1, wherein the content of metastable intermediates is determined at least by one technique selected from the group consisting of: Fourier Transform Infrared Spectroscopy, High Performance Liquid Chromatography, Ultra High Performance Liquid Chromatography, and Trans-metalation reaction.

7. The method of claim 1, wherein the metastable intermediates are metal ion-ligand complexes with a coordination complex that is not the minimal energy coordination complex.

8. The method of claim 1, wherein the metastable intermediates are metal ion-ligand complexes with minimally hydrated ligand coordination groups.

9. The method of claim 1, wherein the macrocyclic chelate is reacted with the lanthanide series metal oxide in water at a temperature from about 60° C. to about 120° C., and for a reaction time from about 12 hours to about 48 hours.

10. The method of claim 1, wherein the aqueous formulation has a free macrocyclic chelate concentration from about 0.0001 to about 0.0600 weight percent.

11. The method of claim 1, wherein the macrocyclic chelate and the lanthanide series metal oxide are reacted in essentially stoichiometric amounts.

12. The method of claim 1, wherein the aqueous formulation comprises less than about 50 parts per million of metastable intermediates.

13. The method of claim 1, wherein the aqueous formulation comprises less than about 50 parts per million of a non-aqueous solvent.

14. The method of claim 1, wherein the lanthanide series metal ion:macrocyclic chelate complex is reacted with the base at a temperature and time until the complex is buffered to a pH of about 7.1 to about 7.6.

15. The method of claim 1, wherein step (a) is accelerated by light at a wavelength of 400 nm to 800 nm wavelength light, a catalyst, ultrasonic sound, or combinations thereof.

16. The method of claim 1, wherein the base is selected from the group consisting of: meglumine, sodium hydroxide, protonated amines, water, alkynes, amines, and alkanes.

17. The method of claim 1, further comprising: removing metastable intermediates from the reaction by an acid-phosphate precipitation method, a negative ionic resin precipitation method, a diethylenetriaminepentacetate (DTPA) addition method, or a cage formation method.

18. The method of claim 17, wherein the cage formation method comprises providing a cyclen molecule and lanthanide series metal ion, capturing the lanthanide series metal ion within the cyclen molecule, and adding carboxylic acid arms sequentially to complex with the lanthanide series metal ion, thereby forming a cage around the lanthanide series metal ion.

19. The method of claim 1, further comprising: controlling the content of metastable intermediates by forming bi-chelate metastable-free lanthanide series metal ion:macrocyclic chelate complexes, wherein the lanthanide series contrast agent has less than about 500 parts per million of the bi-chelate metastable-free lanthanide series metal ion:macrocyclic chelate complexes.

20. The method of claim 19, wherein the bi-chelate metastable-free lanthanide series metal oxide:macrocyclic chelate complexes comprise DOTA-Gd-DOTA complexes.

21. The method of claim 19, wherein the bi-chelate metastable-free lanthanide series metal oxide:macrocyclic chelate complexes are biocompatible contaminants, and not metastable intermediates.

22. The method of claim 19, wherein the DOTA-Gd-DOTA complexes are formed by $Gd^{3+}$ associating with two DOTA molecules, with neither DOTA molecule fully entering the coordination sphere of $Gd^{3+}$.

\* \* \* \* \*